(12) United States Patent
Pappada et al.

(10) Patent No.: US 11,464,456 B2
(45) Date of Patent: Oct. 11, 2022

(54) SYSTEMS AND METHODS TO SUPPORT MEDICAL THERAPY DECISIONS

(71) Applicant: Aptima, Inc., Woburn, MA (US)

(72) Inventors: Scott M. Pappada, Waterville, OH (US); John J. Feeney, Beavercreek, OH (US); William N. DePriest, Dayton, OH (US)

(73) Assignee: Aptima, Inc., Woburn, MA (US)

( * ) Notice: Subject to any disclaimer, the term of this patent is extended or adjusted under 35 U.S.C. 154(b) by 1144 days.

(21) Appl. No.: 15/739,460

(22) PCT Filed: Aug. 7, 2016

(86) PCT No.: PCT/US2016/045938
§ 371 (c)(1),
(2) Date: Dec. 22, 2017

(87) PCT Pub. No.: WO2017/027432
PCT Pub. Date: Feb. 16, 2017

(65) Prior Publication Data
US 2018/0168516 A1 Jun. 21, 2018

Related U.S. Application Data

(60) Provisional application No. 62/202,291, filed on Aug. 7, 2015.

(51) Int. Cl.
*A61B 5/00* (2006.01)
*G16H 50/20* (2018.01)
(Continued)

(52) U.S. Cl.
CPC .............. *A61B 5/7275* (2013.01); *A61B 5/00* (2013.01); *A61B 5/412* (2013.01); *G16H 10/60* (2018.01);
(Continued)

(58) Field of Classification Search
CPC ......... A61B 5/7275; A61B 5/00; A61B 5/412; A61B 5/02055; G16H 50/20; G16H 50/30;
(Continued)

(56) References Cited

U.S. PATENT DOCUMENTS

| 5,103,496 A | 4/1992 | Andres et al. |
| 5,633,954 A | 9/1997 | Gupta et al. |

(Continued)

FOREIGN PATENT DOCUMENTS

| KR | 1019980025157 | 7/1998 |
| WO | 2007149533 | 12/2007 |

(Continued)

OTHER PUBLICATIONS

PCT International Search Report and Written Opinion, PCT/US2013/063178, filed Oct. 3, 2013, dated Jan. 28, 2014, Korea. 15 pgs.
(Continued)

*Primary Examiner* — Ryan W Sherwin
(74) *Attorney, Agent, or Firm* — John J. Brooks, III

(57) ABSTRACT

Systems and methods for supporting medical therapy decisions are disclosed that utilize predictive models and electronic medical records (EMR) data to provide predictions of health conditions over varying time horizons. Embodiments also determine a 0-100 health risk index value that represents the "risk" for a patient to acquire a health condition based on a combination of real-time and predicted EMR data. The systems and methods receive EMR data and use the predictive models to predict one or more data values from the EMR data as diagnostic criteria. In some embodiments, the health condition trying to be avoided is Sepsis and the health risk index is a Sepsis Risk Index (SRI). In some embodiments, the predictive models are neural network models such as time delay neural networks.

20 Claims, 15 Drawing Sheets

(51) Int. Cl.
*G16H 50/30* (2018.01)
*G16H 50/50* (2018.01)
*G16H 10/60* (2018.01)
*A61B 5/0205* (2006.01)
*G16H 20/40* (2018.01)
*G16H 80/00* (2018.01)

(52) U.S. Cl.
CPC .............. *G16H 50/20* (2018.01); *G16H 50/30* (2018.01); *G16H 50/50* (2018.01); *A61B 5/02055* (2013.01); *G16H 20/40* (2018.01); *G16H 80/00* (2018.01)

(58) Field of Classification Search
CPC ........ G16H 50/50; G16H 10/60; G16H 20/40; G16H 80/00
See application file for complete search history.

(56) References Cited

U.S. PATENT DOCUMENTS

| | | |
|---|---|---|
| 5,727,128 A | 3/1998 | Morrison |
| 5,845,254 A | 12/1998 | Lockwood et al. |
| 6,012,034 A | 1/2000 | Hamparian et al. |
| 6,272,480 B1 | 8/2001 | Tresp et al. |
| 6,379,301 B1 | 4/2002 | Worthington et al. |
| 6,544,212 B2 | 4/2003 | Galley et al. |
| 6,572,545 B2 | 6/2003 | Knobbe et al. |
| 6,582,366 B1 | 6/2003 | Porumbescu |
| 6,601,053 B1 | 7/2003 | Schaffer et al. |
| 6,658,396 B1 | 12/2003 | Tang et al. |
| 6,882,940 B2 | 4/2005 | Potts et al. |
| 6,923,763 B1 | 8/2005 | Kovatchev et al. |
| 6,931,327 B2 | 8/2005 | Goode, Jr. et al. |
| 7,025,425 B2 | 4/2006 | Kovatchev et al. |
| 7,052,472 B1 | 5/2006 | Miller et al. |
| 7,230,529 B2 | 6/2007 | Ketcherside, Jr. et al. |
| 7,296,005 B2 | 11/2007 | Minamino et al. |
| 8,655,822 B2 | 2/2014 | Levchuk et al. |
| 8,762,306 B2 | 6/2014 | Cameron et al. |
| 9,076,107 B2 | 7/2015 | Cameron et al. |
| 10,783,801 B1 | 9/2020 | Beaubien et al. |
| 11,081,234 B2 | 8/2021 | Pappada |
| 2003/0028089 A1 | 2/2003 | Galley et al. |
| 2003/0060690 A1 | 3/2003 | Jelliffe et al. |
| 2003/0153821 A1 | 8/2003 | Berner et al. |
| 2003/0175806 A1 | 9/2003 | Rule et al. |
| 2004/0167418 A1 | 8/2004 | Nguyen et al. |
| 2005/0119540 A1 | 5/2005 | Potts et al. |
| 2005/0119534 A1 | 6/2005 | Trost et al. |
| 2005/0171503 A1 | 8/2005 | Berghe et al. |
| 2005/0197554 A1 | 9/2005 | Polcha |
| 2005/0234311 A1 | 10/2005 | Kouchi et al. |
| 2005/0245878 A1 | 11/2005 | Mernoe et al. |
| 2006/0264718 A1 | 11/2006 | Ruchti et al. |
| 2007/0032706 A1 | 2/2007 | Kamath et al. |
| 2007/0078680 A1 | 4/2007 | Wennberg |
| 2007/0208246 A1 | 9/2007 | Brauker et al. |
| 2008/0027292 A1 | 1/2008 | Rosman et al. |
| 2008/0033254 A1 | 2/2008 | Kamath et al. |
| 2008/0082323 A1 | 4/2008 | Bai et al. |
| 2008/0189051 A1 | 8/2008 | Goode et al. |
| 2008/0221923 A1 | 9/2008 | Shogan |
| 2008/0281170 A1* | 11/2008 | Eshelman .............. A61B 5/412 600/301 |
| 2008/0294019 A1 | 11/2008 | Tran |
| 2008/0306353 A1 | 12/2008 | Douglas et al. |
| 2009/0105573 A1 | 4/2009 | Malecha et al. |
| 2009/0150183 A1 | 6/2009 | Schmitt et al. |
| 2009/0156924 A1 | 6/2009 | Shariati et al. |
| 2009/0163776 A1* | 6/2009 | Inbar .................... A61B 5/412 600/301 |
| 2009/0177143 A1 | 7/2009 | Markle et al. |
| 2009/0192366 A1 | 7/2009 | Mensinger et al. |
| 2009/0192722 A1 | 7/2009 | Shariati et al. |
| 2009/0305214 A1 | 12/2009 | Pybus et al. |
| 2010/0114237 A1 | 5/2010 | Giftakis et al. |
| 2010/0280348 A1 | 11/2010 | Wenzel et al. |
| 2010/0291604 A1 | 11/2010 | Rosman et al. |
| 2010/0292634 A1 | 11/2010 | Kircher et al. |
| 2010/0324936 A1* | 12/2010 | Vishnubhatla ......... G06Q 50/22 715/810 |
| 2011/0016067 A1 | 1/2011 | Levchuk et al. |
| 2011/0178820 A1 | 7/2011 | Soni et al. |
| 2011/0225112 A1 | 9/2011 | Cameron et al. |
| 2012/0265549 A1* | 10/2012 | Virolainen ............. G16H 50/70 705/2 |
| 2012/0277833 A1 | 11/2012 | Gerber et al. |
| 2013/0293844 A1 | 11/2013 | Gross et al. |
| 2013/0317834 A1 | 11/2013 | Ryan et al. |
| 2014/0304204 A1 | 10/2014 | Cameron et al. |
| 2015/0012844 A1 | 1/2015 | Paulik et al. |
| 2015/0025329 A1* | 1/2015 | Amarasingham ...... G16H 40/67 600/301 |
| 2015/0095056 A1* | 4/2015 | Ryan ..................... G16H 50/70 705/2 |
| 2015/0193583 A1 | 7/2015 | McNair et al. |
| 2015/0227710 A1 | 8/2015 | Pappada |
| 2015/0248613 A1* | 9/2015 | Harris ..................... G01N 5/04 706/46 |

FOREIGN PATENT DOCUMENTS

| | | |
|---|---|---|
| WO | 2008131224 | 10/2008 |
| WO | 2010019919 | 2/2010 |
| WO | 2011/060398 A1 | 5/2011 |
| WO | 2013126144 | 8/2013 |
| WO | 2014055718 | 4/2014 |
| WO | 2017027432 | 2/2017 |

OTHER PUBLICATIONS

Chubb, Mikayla, Office Action Detail for U.S. Appl. No. 13/058,673, filed Feb. 11, 2011, dated Jul. 25, 2013, USA. 24 pgs.
PCT International Search Report and the Written Opinion, PCT/US2009/53943 filed Aug. 14, 2009, dated Dec. 24, 2009, 6 pgs.
PCT International Preliminary Report on Patentability, PCT/US2009/53943 filed Aug. 14, 2009, dated Feb. 24, 2011, 14 pgs.
Ivanov et. al. 'Temporal Processing Neural Networks for Speech Recognition' In: International Conference on Neural Networks and Artificial Intelligence. Fig. 2 and p. 4, col. 1, para (4), p. 5, col. 1, para (2), p. 7, col. 1, para (7), and p. 8, col. 1, para (4), 9 pgs.
Magoulas et. al. 'Effective Backpropagation Training with Variable Stepsize'. Neural Networks, vol. 10, No. 1, pp. 69-82, 1997, 14 pgs.
Skevofilakas et. al. A Communication and Information Technology Infrastructure for Real Time Monitoring and Management of Type 1 Diabetes Patients. In: Engineering in Medicine and Biology Society, 2007. Aug. 22-26, 2007 pp. 3685-3688.
Pappada, Scott et. al. "Neural Network Prediction of Glucose in Diabetic Patients Using Continuous Glucose Monitoring (CGM) and an Electronic Intensive Life Event Diary (EILED)", 2006, Department of Bioengineering, University of Toledo, Toledo, Ohio and Northeastern Ohio Universities College of Medicine, Rootstown, Ohio, one (1) page poster, USA.
Chubb, Mikayla, Notice of Allowance and Fees Due, U.S. Appl. No. 13/058,673, dated Jan. 31, 2014, USPTO, Arlington VA, USA, 6 pgs.
Chubb, Mikayla, Notice of Allowance and Fees Due, U.S. Appl. No. 14/284,975, filed May 22, 2014, dated Mar. 10, 2015, USPTO, US, pp. 10.
Chubb, Mikayla, Office Action Summary, U.S. Appl. No. 14/284,975, filed May 22, 2014, dated Nov. 5, 2014, 11 pgs.
Becamel, Philippe, International Preliminary Report on Patentability, parent PCT App. No. PCT/US13/063178, dated Apr. 7, 2014, Switzerland, 11 pgs.
Klaus Prank et. al. Predictive neural networks for learning the time course of blood glucose levels. Neural Comp, 1998; 10(4):941-953. Entire document, especially Figs. 1-2 and p. 943, para (2), p. 944, para (4), p. 945, para (1), p. 950, para (3), Cambridge MA, USA, 13 pgs.

(56) References Cited

OTHER PUBLICATIONS

Volker Tresp et al., Neural Network Models for the Blood Glucose Metabolism of a Diabetic, IEEE Transaction on Neural Networks, Sep. 1999, vol. 10 Issue 5, Piscataway NJ, USA, 24 pgs.
Wong, Lee W., Written Opinion of the International Searching Authority, PCT App. No. PCT/US16/45938, dated Oct. 24, 2016, 14 pages, US.
Patel, Neha, Office Action Summary, U.S. Appl. No. 14/433,501, filed Apr. 30, 2015, dated Sep. 15, 2017, 26 pgs.
Patel, Neha, Office Action Summary, U.S. Appl. No. 14/433,501, filed Apr. 30, 2015, dated Mar. 8, 2018, 33 pgs.
Ferrer, Richard et. al. "Empiric Antibiotic Treatment Reduces Mortality in Severe Sepsis and Septic Shock From the First Hour: Results From a Guideline-Based Performance Improvement Program*", Crit Care Med. Aug. 2014;42 (8):1749-55, USA, 7 pgs.
Henry, Katharine et. al. "A targeted real-time early warning score (TREWScore) for septic shock", Science Translational Medicine Aug. 5, 2015: vol. 7, Issue 299, pp. 299ra122, 10 pgs.
Donegan, Lee-Ann, "Penn Medicine's "Sepsis Sniffer" Generates Faster Sepsis Care and Suggests Reduced Mortality", Perelman School of Medicine, Pennsylvania, USA, 2 pgs.
Klein, K. J., & Kozlowski, S. W. (2000). A multilevel approach to theory and research in organizations: Contextual, temporal, and emergent processes. In K. J. Klein & S. W. J. Kozlowski (Eds.), Multilevel theory, research, and methods in organizations: Foundations, extensions, and new directions (pp. 3-90). San Francisco, CA: Jossey-Bass. 45 pgs.
Evans, J. S. B. T., & Stanovich, K. (2013). Dual-process theories of higher cognition: Advancing the debate. Perspectives in Psychological Science, 8(3), 223-241. 19 pgs.
Olguín, D. O., Waber, B. N., Kim, T., Mohan, A., Ara, K., & Pentland, A. (2009). Sensible organizations: Technology and methodology for automatically measuring organizational behavior. IEEE Transactions on Systems, Man, and Cybernetics, Part B (Cybernetics), 39(1), 43-55. 13 pgs.
Kamzanova, A. T., Kustubayeva, A. M., & Matthews, G. (2014). Use of EEG workload indices for diagnostic monitoring of vigilance decrement. Human factors, 56(6), 1136-1149. 14 pgs.
Berka, C., Levendowski, D. J., Lumicao, M. N., Yau, A., Davis, G., Zivkovic, V. T., & Craven, P. L. (2007). EEG correlates of task engagement and mental workload in vigilance, learning, and memory tasks. Aviation, space, and environmental medicine, 78(5), B231-B244. 14 pgs.
Kohlmorgen, J., Dornhege, G., Braun, M., Blankertz, B., Müller, K. R., Curio, G., & Kincses, W. (2007). Improving human performance in a real operating environment through real-time mental workload detection. Toward Brain-Computer Interfacing, 409-422. 14 pgs.
Moreno, R. (2010). Cognitive load theory: More food for thought. Instructional Science, 38(2), 135-141. 7 pgs.
Gaba, D. M., & Raemer, D. (2007). The tide is turning: organizational structures to embed simulation in the fabric of healthcare. Simul Healthcare 2007;2: 1-3. 3 pgs.
Niehaus, J., & Riedl, M. O. (2009). Scenario adaptation: An approach to customizing computer-based training games and simulations. In Proceedings of the AIED 2009 Workshop on Intelligent Educational Games (vol. 3, pp. 89-98). 10 pgs.
Paas, F., Renkl, A., & Sweller, J. (2003). Cognitive load theory and instructional design: Recent developments. Educational psychologist, 38(1), 1-4. 4 pgs.
Vygotsky, L. (1978). Interaction between learning and development. Readings on the development of children, 23 (3), 34-41. 7 pgs.
Ivanova, A., & Dyankova, E. (2009) Designing a Decision Engine for Adaptive Training Simulators. Proceedings of e-Learning, 9, 207-213. 7 pgs.
Olguin, D. O., Gloor, P. A., & Pentland, A. S. (2009). Capturing individual and group behavior with wearable sensors. In Proceedings of the 2009 aaai spring symposium on human behavior modeling, SSS (vol. 9). 7 pgs.
Olguín-Olguín, D., & Pentland, A. (2010). Sensor-based organisational design and engineering. International Journal of Organisational Design and Engineering, 1(1-2), 69-97. 29 pgs.
Salas, Eduardo, Rosen, Michael A. , Held , Janet D., Weissmuller, Johnny J. (2009) Performance Measurement in Simulation-Based Training: A Review and Best Practices. Simulation Gaming 2009. 49 pgs.
Gevins, A., & Smith, M. E. (2003). Neurophysiological measures of cognitive workload during human-computer nteraction. Theoretical Issues in Ergonomics Science, 4(1-2), 113-131. 20 pgs.
Lei, S., & Roetting, M. (2011). Influence of task combination on EEG spectrum modulation for driver workload estimation. Human factors, 53(2), 168-179. 12 pgs.
Funke, G. J., Knott, B. A., Salas, E., Pavlas, D., & Strang, A. J. (2012). Conceptualization and measurement of team workload: A critical need. Human Factors, 54(1), 36-51. 16 pgs.
Oser, R. L., Cannon-Bowers, J. A., Salas, E., & Dwyer, D. J. (1999). Enhancing human performance in technology-rich environments: Guidelines for scenario-based training. Human Technology Interaction in Complex Systems, 9, 175-202. 28 pgs.
Pappada SM, Feeney JJ, Moffat-Bruce SM., Winfield S, Papadimos TJ, A novel measurement technology to improve critical care provider performance and skill acquisition, Society of Critical Care Medicine 46th Critical Care Congress Honolulu, HI, Jan. 2017. 9 pgs.
Pappada SM, Papadimos TJ, Lipps J, Feeney JJ, Durkee KT, Galster SM, Winfield S, Pfeil S, Castellon-Larios K, Bhandary SB, Stoicea N, Moffat-Bruce SM. Establishing an instrumented environment for simulation-based training of healthcare providers: an initial proof of concept. International Journal of Academic Medicine, Jul. 2016. 124 pgs.
Wittman-Regis, Agnes, International Preliminary Report on Patentability for International Pat. App. No. PCT/US2016/045938, dated Feb. 22, 2018. 8 pgs.
Chubb, MicKayla, Restriction Requirement for U.S. Appl. No. 13/058,673, filed Feb. 11, 2011, dated Apr. 9, 2013, USA. 7 pgs.
Pappada et al., Response to Non-Final Rejection with Affidavit for U.S. Appl. No. 13/058,673, dated Nov. 25, 2013, 73 pgs., USPTO, Arlington, VA, US.
Reichert, Rachelle, Advisory Action Detail for U.S. Appl. No. 14/433,501, filed Apr. 3, 2015, dated Jun. 8, 2018 USA. 5 pgs.
Reichert, Rachelle, Office Action Detail for U.S. Appl. No. 14/433,501, filed Apr. 3, 2015, dated Jan. 17, 2019, USA. 27 pgs.
Reichert, Rachelle, Office Action Detail for U.S. Appl. No. 14/433,501, filed Apr. 3, 2015, dated Aug. 21, 2019, USA. 28 pgs.
Reichert, Rachelle, Advisory Action Detail for U.S. Appl. No. 14/433,501, filed Apr. 3, 2015, dated Nov. 14, 2019, USA. 4 pgs.
Reichert, Rachelle, Office Action Detail for U.S. Appl. No. 14/433,501, filed Apr. 3, 2015, dated May 29, 2020, USA. 31 pgs.
Reichert, Rachelle, Office Action Detail for U.S. Appl. No. 14/433,501, filed Apr. 3, 2015, dated Dec. 9, 2020, USA. 34 pgs.
Reichert, Rachelle, Notice of Allowance for U.S. Appl. No. 14/433,501, filed Apr. 3, 2015, dated Mar. 30, 2021, USA. 17 pgs.
McClellan, James, Office Action Detail for U.S. Appl. No. 15/850,998, filed Dec. 21, 2017, dated Feb. 5, 2020. 14 pages.
McClellan, James, Notice of Allowance, U.S. Appl. No. 15/850,998, filed Dec. 21, 2017, dated May 14, 2020. 5 pages.
McClellan, James, Office Action Detail for U.S. Appl. No. 17/024,325, filed Sep. 17, 2020, dated Mar. 15, 2022. 19 pages.
Tervonen et al., "A Stochastic multicriteria model for evidence-based decision making in drug benefit-risk analysis", Statistics in Medicine, vol. 30, pp. 1419-28, Jan. 26, 2011.

* cited by examiner

| Vital Sign | Model Type | MAD% (1 hr) | MAD% (2 hr) | MAD% (3 hr) |
|---|---|---|---|---|
| Heart Rate | Leave one out | 11.74 | 14.84 | 16.08 |
| Heart Rate | Model Fit | 5.30 | 5.97 | 6.47 |
| Respiration Rate | Model Fit | 15.68 | 17.62 | 18.03 |
| Temperature | Model Fit | 0.95 | 1.14 | 1.37 |
| Mean Arterial Pressure | Model Fit | 9.59 | 10.27 | 10.49 |
| Systolic Blood Pressure | Model Fit | 7.39 | 8.15 | 9.64 |
| Urine Output | Model Fit | 67.66 | 81.64 | 83.54 |

FIG. 6A

| EMR Data Source | Upper Threshold | Lower Threshold |
|---|---|---|
| Heart Rate (beats/min) | 130.0 (tachycardia) | N/A |
| Respiration Rate (breaths/min) | 20.0 (tachypnea) | N/A |
| Temperature (°C) | 38.3 (hyperthermia) | 36.0 (hypothermia) |
| Platelet Count ($\mu L^{-1}$) | N/A | 100,000 (thrombocytopenia) |
| White Blood Cell Count ($\mu L^{-1}$) | 12,000 (leukocytosis) | 4,000 (leukopenia) |
| Urine Output (mL/kg/hr) | N/A | 0.5 (acute oliguria) |
| Creatinine Increase (mg/dl) | 0.5 | N/A |
| Blood Glucose with Dx of DM (mg/dl) | 150 | 70* |
| Systolic Blood Pressure (mmHg) | N/A | 90 |
| Mean Arterial Pressure | N/A | 60 |
| Lactate (mmol/L) | 2.0 (hyperlactatemia) | |
| Glasgow Coma Scale | N/A | <15 (altered mentation) |

FIG. 6B

SYSTEMS AND METHODS TO SUPPORT MEDICAL THERAPY DECISIONS

CROSS-REFERENCE TO RELATED APPLICATIONS

This application claims benefit of U.S. App. No. 62/202,291 filed Aug. 7, 2015 entitled "SYSTEMS AND METHODS TO SUPPORT MEDICAL THERAPY DECISIONS" and the content of which is herein incorporated by reference in its entirety.

STATEMENT REGARDING FEDERALLY SPONSORED RESEARCH OR DEVELOPMENT

The invention was made with Government support under Contract Numbers W81XWH-15-C-0017 and W81XWH-16-C-0003 both awarded by the U.S. Army. The Government has certain rights in the invention.

REFERENCE TO SEQUENCE LISTING, A TABLE, OR A COMPUTER PROGRAM LISTING COMPACT DISC APPENDIX

Not Applicable.

BACKGROUND OF THE INVENTION

1. Field of the Invention

This invention relates to support system to assist medical treatment decisions, in particular this invention relates to providing specific support information through the use of predictive models.

2. Description of the Prior Art

In the field of medicine, it is known there is a problem with optimizing the timing of antibiotic therapy (i.e. onset time, dosing values, and ongoing management) which is critical to improving patient outcomes. The risk of mortality in patients with severe sepsis or septic shock may increase significantly with as little as a one hour delay in antibiotic administration. Early and accurate prediction of sepsis or septic shock prior to its on-set would benefit the field of medicine. Optimal healthcare delivery in critical care settings benefits from simultaneous monitoring of multiple organ systems and rapid responsiveness to a patient's ever-changing physiological status. Multi-system organ failure as a result of infection is a common scenario in acute care settings. In this high acuity environment, medical decisions are made by a critical care team directed by an intensivist (critical care physician) or even another potentially less-trained individual. The optimal treatment and mitigation of serious infections which arise in patients within the Intensive Care Unit (ICU) remains a persistent problem facing all healthcare professionals in the critical care setting. Appropriate, timely, and effective antibiotic therapy is vital to the management of infection in both military and civilian critical care settings and leads to significant reductions in morbidity and mortality, cost savings, a decrease in both resistant organisms and serious secondary superinfections.

Currently there exist a number of internationally recognized standards for treatment of infection in critically ill patient populations. Treatment of sepsis, for example, can involve multiple interventions including but not limited to: fluid resuscitation (including transfusion of blood products), use of vasopressors and inotropes, maintenance of glycemic control, use of corticosteroids, invasive monitoring, and in many situations mechanical ventilation or even extracorporeal support. The choice of antibiotic for empirical treatment of infections is very "institution specific" and is encoded in antibiograms generated annually for specific units within a healthcare institution (e.g. ICU versus non-ICU). The antibiogram contains information on identity and susceptibility patterns (to a particular antibiotic) of bacteria commonly isolated within a particular unit.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

In some embodiments, a method of supporting medical therapy decisions, the method comprising receiving electronic medical record (EMR) data and predicting one or more EMR data values from the EMR data. In some embodiments, the method further comprises determining a risk index from the EMR data and the EMR data values. In some embodiments, the risk index is a Sepsis risk index.

In one example embodiment, a processor based method of supporting medical therapy decisions is provided, the method comprising receiving electronic medical record (EMR) data and predicting one or more data value from the EMR data at at least two future patient states from a current patient state. In some embodiments, the at least two future patient states comprise the future patient state at one, two, and three hour time horizons from the current patient state. In some embodiments, predicting one or more data values from the EMR data comprises predicting the data values with a time-delay neural network model utilizing a history of EMR/patient-specific data and current data. In some embodiments, each EMR data source has a predictive model for each of three time horizons. In some embodiments, the one or more data values from the EMR data comprises values of a diagnostic criteria for sepsis. In some embodiments, the methods further comprise determining a risk index. In some embodiments, the risk index comprises a 0-100 Sepsis Risk Index (SRI) and the SRI comprises a representation of a risk for a patient to acquire sepsis.

In some embodiments, the methods further comprise determining a weighted factor value of a weighted data type for each of the current patient state and the at least three future patient states, determining an unweighted factor value of an unweighted data type for each of the current patient state and the at least three future patient states, normalizing the weighted factor value and the unweighted factor value for each of the current patient state and the at least three future patient states as a risk index for each of the current patient state and the at least three future patient states and normalizing the risk index for each of the current patient state and the at least three future patient states as the overall risk index. In some embodiments, the weighted data type comprises one or more of the EMR data selected from the group of a heart rate, a respiration rate, a systolic blood pressure, a mean arterial pressure, a temperature and a urine output. In some embodiments, the unweighted data type comprises one or more of the EMR data selected from the group of a blood glucose level, a white blood cell count, a creatinine level, a platelet count and a lactate level.

In one example embodiment, a processor based method of identifying a therapy risk is provided, the method comprising receiving EMR data comprising EMR data values of at least two EMR data types, predicting a first predicted value of each of the at least two EMR data types at a first time horizon, comparing each of the first predicted values to a threshold for each of the at least two EMR data types, determining a first risk index value for each of the at least two EMR data types at the first time horizon, normalizing each of the first risk index values to an overall risk index value to identify the therapy risk. In some embodiments, the overall risk index value may be mapped to a therapy risk index and a therapy risk index value to identify the therapy risk. In some embodiments, the overall risk index is a SRI. In some embodiments, one of the two EMR data types is a weighted data type and the other EMR data type is a unweighted data type. In some embodiments, the method further comprises determining a current risk index value of the at least two EMR data types at a current time, predicting a second and a third predicted value of each of the at least two EMR data types at a second and a third time horizon respectively, comparing each of the second and the third predicted values to the threshold for each of the at least two EMR data types, determining a second and a third risk index value for each of the at least two EMR data types at the second and the third time horizon respectively, normalizing each of the current, the first, the second and the third risk index values to the overall risk index value to identify the therapy risk.

In one example embodiment, a graphic user interface is provided to support medical therapy decisions for a patient at a health care facility, the user interface comprising an EMR window configured to display EMR data values of EMR data the patient, a predictive model window configured to display predicted EMR data values of the patient, a risk index window configured to display a risk index value and an access interface configured to provide access to an antibiogram of the health care facility. In some embodiments, the risk index is a SRI.

In some embodiments, the EMR data comprises one or more of a heart rate, a respiration rate, a systolic blood pressure, a mean arterial pressure, a temperature and a urine output. In some embodiments, the EMR data further comprises a blood glucose level, a white blood cell count, a creatinine level, a platelet count and a lactate level.

BRIEF DESCRIPTION OF THE SEVERAL VIEWS OF THE DRAWINGS

A more particular description of the invention will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A shows example predictive model performance using USAISR EMR dataset;

FIG. 6B shows example EMR data sources and corresponding thresholds for calculating a Sepsis Risk Index (SRI);

DETAILED DESCRIPTION OF THE INVENTION

Figure 1A:
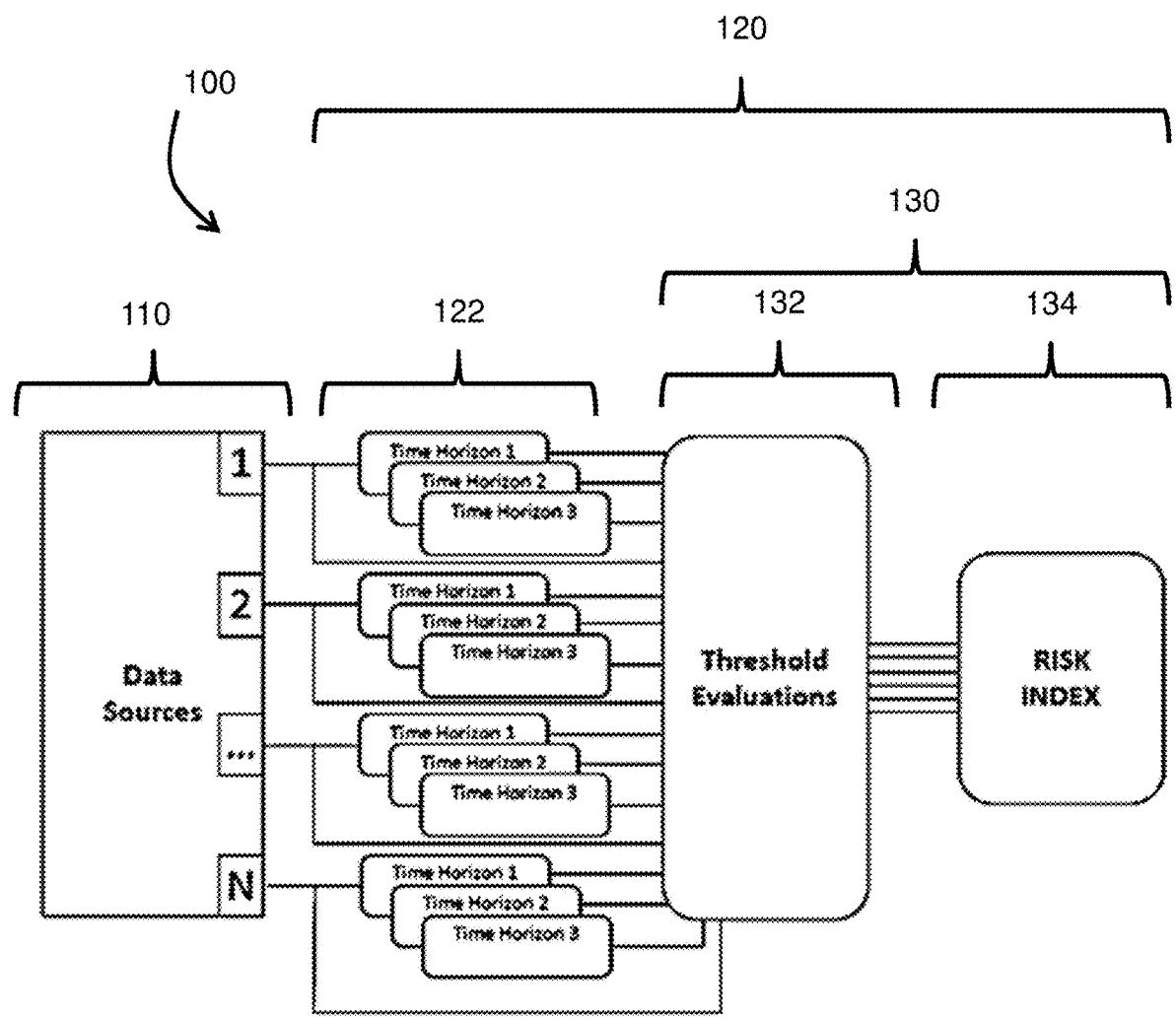
FIG. 1A shows a high-level functional diagram of one example embodiment of systems and methods to support medical therapy decisions.

Systems and methods to support medical therapy decisions will now be described in detail with reference to the accompanying drawings. It will be appreciated that, while the following description focuses on a system that supports antibiotic therapy decisions based on when the patient is predicted to be or trending towards (as indicated by prediction of vital signs and key data sources) sepsis, the systems and methods disclosed herein have wide applicability. Notwithstanding the specific example embodiments set forth below, all such variations and modifications that would be envisioned by one of ordinary skill in the art are intended to fall within the scope of this disclosure.

Embodiments of systems and methods to support medical therapy decisions recognize shortcomings in the solutions currently available in the medical field. The field's current solution to support recognizing and treating infections, the institution's annual antibiogram, can often exist outside of the electronic medical records (EMR) system, and as a result, key patient-specific factors that may require modification of antibiotic selection and treatment are not easily integrated. Concurrent medications administered, organ system affected/infected, organ failure (i.e., liver, renal), age, severity of illness, etc., all play a role in the decision to prescribe or recommend a specific antibiotic and its dosing regimen in a specific patient. Due to the ongoing and unpredictable variations in the status of critically ill patients, embodiments of the disclosed systems and methods recognize that assessment of antibiotic type and its regimen should be undertaken daily. Furthermore, caring for multiple patients with multiple serious physiological disturbances is not only daunting, but can be overwhelming even for the experienced clinician. And monitoring data inputs from multiple electronic and non-electronic sources can cause delays or errors in the appropriate, timely, and effective delivery of antibiotics to the infected or septic patient.

Optimization of antibiotic therapy in terms of timing (i.e., onset of therapy and initial dose) and appropriate antibiotic selection for a given infection source/organism are extremely important. Studies have shown that there is a statistically significant increase in the mortality associated with the number of hours of delay at the initiation of antibiotic therapy. Mortality has been shown to increase significantly in patients with severe sepsis and septic shock after as little as a single hour delay in time to antibiotic administration. Overutilization and inappropriate selection of antibiotics is also a critical and pervasive problem within the critical care setting. This leads to unfortunate consequences including, but not limited to: microbial resistance, superinfections including *Clostridium difficile*, increased healthcare costs resultant of unnecessary or inappropriate antibiotic use, and compromised patient safety and outcomes. Further complicating this issue is that the ICU is an extremely data-intensive environment where the data needed for optimal situational awareness to support intelligent and directed antibiotic therapy is distributed across a number of different sources without a common IT and EMR infrastructure (e.g. antibiograms not within or not having access to EMR systems). To identify and interpret each relevant data source is time-consuming and may result in cognitive overload in even the most experienced healthcare professionals.

There is a significant benefit from a comprehensive decision support system which integrates all pertinent data sources related to antibiotic delivery into single stand-alone and intelligent platform. Such a tool may not only provide healthcare personnel a decision support aide but also make available the necessary information and context to ensure trust in their decision-making and empower them to enhance patient safety and care. Solutions that have been used to address this problem in the past include Systemic inflammatory response syndrome (SIRS) and American Burn Association (ABA) criteria predict sepsis in the burn patients which are established guidelines that physicians use. Research in this area identified novel predictors of sepsis that have been shown to outperform American Burn Association sepsis criteria in burn intensive care unit patients. Additionally, the sepsis sniffer from University of Pennsylvania's Perelman School of Medicine uses laboratory and vital-sign data in the electronic health record of hospital inpatients to identify those at risk for sepsis in an attempt to automate the identification of sepsis risk.

The disclosed solution addresses shortcomings found in existing solutions by: (1) providing predictive models using electronic medical records (EMR) data with varying time horizons that form the diagnostic criteria for sepsis, and (2) deriving a numeric risk index that represents a "risk" for a patient undergoing a therapy based on a combination of real-time and predicted EMR data. In some embodiments, the risk index is a Sepsis Risk Index (SRI) that represents the "risk" for a patient to acquire sepsis during therapy. In some embodiments the SRI is a numeric range of 1-100. This combination of predicted and current values for diagnostic criteria is a novel and unique approach. With the disclosed solution, the prediction of sepsis risk supports earlier intervention and consequently more effective administration of antibiotics over existing solutions.

Embodiments of the disclosed systems and methods provide intelligent and directed decision support and alerts while taking into account the many relevant EMR data points and patient specific factors which are required for optimal antibiotic therapy and infection management. These systems combine intelligent visualization of EMR data and patient specific factors with advanced predictive models to provide healthcare personnel the necessary information and context on one platform. These systems ensure trust in decision-making and empowers healthcare providers to enhance overall patient safety and care.

The disclosed solution provides time horizon predictions allowing assessment of a penalty function (e.g., high SRI) not only when current values of EMR data are out of bounds of the sepsis diagnostic criteria, but also when predicted values exceed diagnostic criteria values.

One Example Embodiment of Methods to Support Medical Therapy Decisions:

In one example embodiment, methods to support medical therapy decisions generally comprise the steps of receiving medical data of a patient from a data source, predicting multiple time horizon values of that data, comparing the predicted values of the data to thresholds to determine a data type risk value and normalizing these data type risk index values to create an overall risk index value such as a therapy risk index value.

As shown in the functional diagram of FIG. 1A, the methods to derive a therapy risk index value generally comprises the steps providing multiple data sources representing patient state at 110, predicting future values of this data at 122 and determining a risk index value at 130.

Generally, the patient data sources are provided at 110 to determine predictive therapy data at 120. The predictive therapy data may determine a risk index at 120 by generating multiple time horizon predictions of the data at 122. The multiple time horizon predictions are made by predictive models that: (1) provide prediction of key data sources which are diagnostic criteria for a therapy, and (2) derive a risk index representing the "risk" for a patient to acquire negative results based on real-time and predicted patient data. The multiple time horizon predictions of the data at 122 may be used as input to determine the risk index at 130 by comparing the data to thresholds at 132 and determining the risk index at 134.

In some embodiments, the predictive models are neural network models that predict future values of the data sources and these future values are used as diagnostic criteria for the risk index. These neural network models generally comprise any type of algorithm configured to use the observed values of a data source at discrete times to accurately predict the value of the data source at some set of prediction time steps in the future.

In a preferred embodiment, the data source is an EMR data source and the neural network model is a time delay neural network. The general form for a time delay neural network is:

$$y(t) = \left(\sum_{i=1}^{N} w_i \delta_i(t - d_i)\right) * x(t) = \sum_{i=i}^{N} w_i x_i(t - d_i),$$

where y is the resulting predicted values generated, w is the matrix of network weights, δ is a delta function, d is the time delays, t is time, x represents the input values of the EMR data source and i represents a number of increments. The EMR data source comprises values for data such as, but not limited to a heart rate a respiration rate, a systolic blood pressure, a mean arterial pressure, a temperature, a urine output, glucose, etc. and the time delay neural network maintains a history of model inputs via tap delay lines that store a current real-time EMR input data vector and N (desired history to be used for the neural network model) historical EMR data vectors. The neural network also consists of N hidden layers and a single output layer. In one embodiment the neural network is trained via backpropagation where optimal network weights (w) are identified via the Levenberg-Marquardt algorithm. These weights are used in the above equation for a time delay neural network.

The risk index is based on real-time changes that occur in current and predicted data sources and is calculated by an algorithm to derive a risk index value on a predefined scale, such as a 0-100 scale, based on real-time changes that occur in the data and the predictions derived from the predictive models described above. The risk index is derived by evaluating whether the current data values and predicted values are within desirable ranges (i.e. not indicating patient is in risk state or is trending towards risk state) by comparing these values to threshold values. In some embodiments, calculating the risk index comprises taking the total count of available data sources is calculated and each data source (or predicted data source) is evaluated with respect to thresholds values (predefined as indicators for risk). The risk index is designed to increase more rapidly if data sources exceed threshold values across the model prediction horizon. To accomplish this, a "penalty" is applied during calculation of the risk index if the patient status persists or evolves towards a risk-state over time. As such the risk index algorithm consists of a series of logical operations to determine whether current and predicted data sources exceed the threshold values. If the data sources do exceed the threshold defined for a specific data source, the risk index is incremented by a risk factor weighted value $W_i$ where $W_i$ influences the contribution of that specific data source to the risk index. The weight factor is larger for some specific data sources and if values of the data sources persists out of range over time (i.e. across the model prediction horizon).

In some embodiments, patient specific data sources are made available and the current value and historical values are presented to a set of three time-delay neural network models to generate predictive values for each data source. A different predictive model may be used for each of the three time horizons. The predictive models are used to predict future trends/changes in data at different time intervals over a prediction horizon from a current real-time patient state. The current and predictive data source values are then compared against threshold values specific to each data source.

In some embodiments, the predictive models for predicting changes for these relevant data sources use a prediction horizon of about three hours. The predictive models are designed to predict future trends/changes in data sources at one, two, and three hours from a current real-time patient state (where state comprises all current real-time data source values and patient-specific data source values). The predictive models may be implemented with time-delay neural network models which utilize a history of data source and patient-specific data as well as current data to generate predictions. Each data source may have a predictive model for each of the three time horizons.

For a prediction, the longer the time horizon, typically the greater the uncertainty in the estimated value. However, even though embodiments utilize multiple time horizons, accurate predictions of patient state can be determined because the time delay neural networks predicating those trajectories account for these time horizons independently thus minimizing the uncertainty even for the longer time horizons. Additionally, given the penalty function with the risk index algorithm the longer a patient's input variables are predicted to exceed the risk criteria, the greater their impact on the risk index.

Figure 1B:
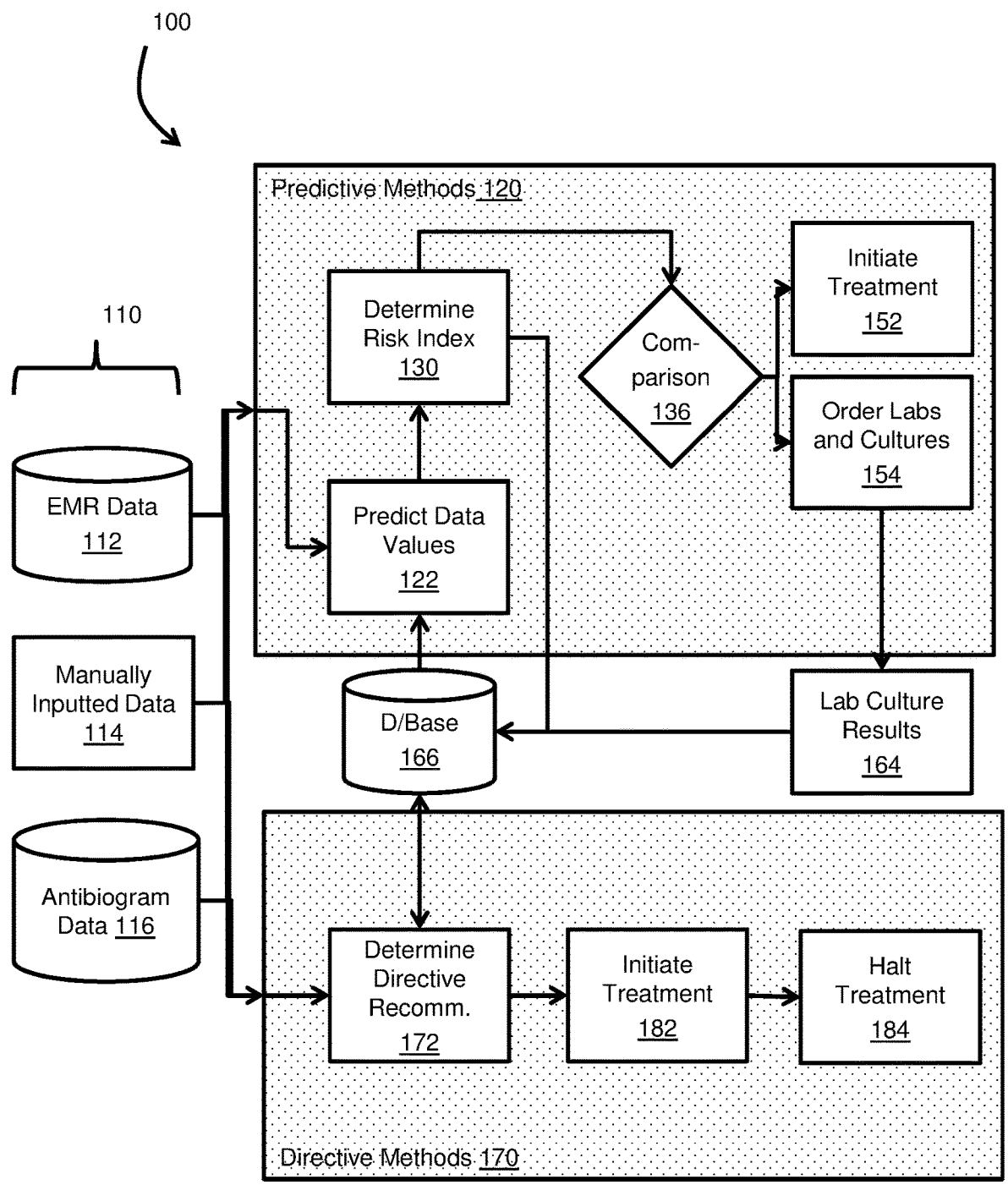
FIG. 1B shows a high-level functional diagram of one example embodiment of a system to support medical therapy decisions including a predictive model and a directive model.

Referring to the functional diagram of FIG. 1B, in some embodiments, the methods may further comprise additional features. FIG. 1B shows an embodiment of the method 100 shown in FIG. 1A including receiving data values from the data sources 110 and using the predicting features 120 to predict future data values at 122 and determine the risk index at 130. The data sources 110 may comprise data sources including EMR data 112, manually inputted data 114 and antibiogram data 116. This embodiment includes making a comparison to a patient population specific risk index threshold at 136 that will determine whether to initiate therapy actions such as initiate treatment at 152 or order labs and cultures at 154. The methods may also include storing system data in a database at 166. The database 166 may store results of the labs and cultures 164 and may be used as additional data input into the overall methods 100 and the predicting of data values at 122. The database 166 may also store information such as utilized data sources, alerts, lab/culture results, system recommendations, user actions and reviews by subject matter experts.

The methods may further include directive recommendation methods to provide supplementary decision support for making medical therapy decisions. Generally, these directive methods provide additional information for the user to make informed decisions on how to treat the patient. FIG. 1B shows an embodiment including these directive recommendation features at 170. In some embodiments, these directive methods at 170 comprise utilizing Self-Organizing Feature Maps (SOFMs)/Kohonen neural network models to determine a directive recommendation at 172. SOFMs are a type of neural network model which is trained using unsupervised learning in order to produce a "map" or discretized representation of the neural network input feature space. Generally, these neural network models function as directive models to suggest a specific therapy at 172, such as to start a specific antibiotic and dosage 182 once laboratory/culture results are reported (i.e. identifying a specific infection source) and/or to halt the treatment at 184. The SOFMs attempt to learn the structure of the input data 110 used in the predictive models 122 and may use additional data such as the specific antibiotic prescribed, its dose and cost.

In applying this SOFM modeling approach within the disclosed system, a training database to generate a SOFM model may have an input feature space consisting of but not limited to: EMR data, patient demographics, patient outcomes, laboratory/culture results, and specifics surrounding antibiotic therapy (antibiotic choice, dosage, dosing intervals/times, antibiotic cost, etc.). When data is received in real-time, an input vector consisting of the aforementioned data will be placed on the map. A node (set of inputs within the generated SOFM) will be identified which is closest to the real-time input vector node via calculating the smallest distance (between weight vectors) between the real-time input node and nodes on in the feature map (SOFM model). The closest node within the map that has the most desirable patient outcome or set of outcomes based on the training database will identify the best antibiotic treatment course to implement (e.g. patient discharged, lowest antibiotic cost, "best" quantifiable response of vitals/patient status to antibiotic treatment).

With a large training database, the SOFMs are able to learn and recognize clusters in the data when new data is presented to the network. The SOFMs either map this input to a recognized cluster or identify it as novel case when there is no cluster identified. The SOFMs function to map directive antibiotic therapy decisions to current and historical/concurrent patient data to enable the prediction of several patient outcomes such as, but not limited to: (1) ICU length of stay, (2) hospital length of stay, (3) in-hospital mortality, (4) thirty day mortality, (5) six month mortality, (6) one year mortality, and two year mortality.

In some embodiments, the SOFM based directive model architecture has access to a list of potential antibiotics that are rank-ordered via rule-based logic and algorithms based on knowledge of key underlying system data sources including but not limited to: hospital unit antibiogram, patient allergies, costs of antibiotics, etc. The directive model inputs representing directive antibiotic treatment decisions (e.g., specific antibiotic, dosage, and delivery type) are varied iteratively, applied against the network weights to identify the most appropriate directive antibiotic therapy intervention leading to the most favorable set of patient outcomes. For example, one potential iteration could increase or decrease antibiotic dosage, these alternative doses applied to determine an optimal dosage.

In one example embodiment, the above methods to support medical therapy decisions use patient specific Electronic Medical Records (EMR) data as the multiple data sources to supply both current and historical data values representing the patient state and the risk index is a Sepsis Risk Index (SRI).

Any type of EMR data may be used in the systems and methods disclosed. To compute the SRI value as the risk index, several different EMR data sources are used to provide EMR data, such as but not limited to: Heart Rate, Respiration Rate, Systolic Blood Pressure, Mean Arterial Pressure, Temperature, Urine Output (e.g., a urine output rate), Blood Glucose (e.g., blood glucose level), White Blood Cell Count, Creatinine (e.g., blood creatinine level), Platelet Count, and Lactate (e.g., blood lactate level). These data sources are used as input to predictive models as they are used to support medical therapy decisions for sepsis.

As described above, the current and predicted values of the EMR data are used to determine if the values exceed normative predefined ranges for those data types. These evaluations comprise a comparison of the current/predicted values to predefined minimum and maximum threshold values for each of the indicators for sepsis. If the current or predicted EMR data values are within desirable ranges, the patient does not indicate they are in a septic state or are trending towards sepsis. If the current or predicted EMR data values exceed thresholds this would be an indication that the patient is either in a septic state or are trending towards sepsis. The SRI value is used as an indicator of the degree to which the patient is in or is trending towards sepsis.

The predetermined threshold may be derived from research identifying predictors and predictor values for the therapy risk to be avoided. In an embodiment to predict risk of sepsis, there are novel predictors of sepsis which have been shown to outperform American Burn Association sepsis criteria in burn intensive care unit patients. These thresholds may be adaptable and customizable for the specific medical therapy to be provided. The thresholds defined in FIG. 6B are well suited for an initial dataset and patient population used for predictive model and Sepsis Risk Index algorithm development. Comparing these values to the predicted values of data from the predictive models provide healthcare staff an indication that a patient's status is evolving towards sepsis. Additionally, when the SRI value exceeds a threshold value, this is an alert for staff to consider initiation of broad spectrum antibiotic therapy. The current SRI threshold defined for alerting system users to consider initiation of broad spectrum antibiotic therapy may be notionally set to 70, however, other thresholds may be defined based on statistical analysis and algorithm performance (i.e. sensitivity/specificity of alerts) from larger patient populations.

In one example embodiment, the algorithm for calculating the SRI value comprises calculating an SRI value (as a risk index value) for separate time horizons and then using a combination of these results as an overall SRI measure (as an overall risk index value). In general, each of the SRI values for the separate time horizons is calculated by normalizing both (1) an unweighted factor and (2) a weighted factor. The unweighted factor is generally a count of the number of unweighted data types that exceed a threshold and the weighted factor is generally a count of the number of weighted data types that exceed a threshold for each of those data types multiplied by the risk factor weighted value $W_i$. These weighted and unweighted factors are normalized by dividing the sum of the unweighted and the weighted factor by the number of unweighted and weighted data types. The risk factor weighted value of the weighted data types serves as a penalty applied during calculation of the SRI value if the patient status persists or evolves towards a sepsis-state over time a longer time horizon. The weighted data types best fit the risk factor weighting because these data types best reflect those data types reflecting the risk of the patient either being in a septic state or are trending towards sepsis.

As an example of calculating an SRI value, in one example embodiment, the four sepsis risk indices are calculated at four time horizons representing 1) real-time sepsis risk, 2) sepsis risk at t+1 (hour), 3) sepsis risk at t+2 (hours), and 3) sepsis risk at t+3 (hours); the unweighted data types comprise one or more of Blood Glucose, White Blood Cell Count, Creatinine, Platelet Count, and Lactate; and the weighted data types comprise one or more of Heart Rate, Respiration Rate, Systolic Blood Pressure, Mean Arterial Pressure, Temperature and Urine Output. In this embodiment, once an available EMR data source's current and predicted values are evaluated with respect to thresholds values, they are used in computing the SRI value for each time horizon (current time, t+1 hour, t+2 hours, and t+3 hours). The current time's SRI value is a count of both the weighted and unweighted data types exceeding threshold values normalized by the total number of available data types used in the threshold evaluations (i.e., weighted value=1). The t+1 hour time horizon SRI value is computed by summing the count of unweighted data types exceeding threshold and the count of weighted data types exceeding threshold multiplied by a risk factor weighted value of about 1.2. That sum is then normalized by dividing the total number of available data types used in the threshold evaluations. The t+2 hour time horizon SRI value is computed by summing the count of unweighted data types exceeding threshold and the count of weighted data types exceeding threshold multiplied by a risk factor weighted value of about 1.5. That sum is then divided by the total number of available data types used in the threshold evaluations. Finally, the t+3 hour time horizon SRI value is computed by summing the count of unweighted data types exceeding threshold and the count of weighted data types exceeding threshold multiplied by a risk factor weighted value of about 1.8. That sum is then divided by the total number of available data types used in the threshold evaluations.

It is understood that although specific risk factor weighted values are disclosed for an algorithm to compute an SRI, alternative risk factor weighted values for each of the time horizons are possible that would provide for an appropriate risk index and risk index values.

The overall SRI value may be determined by accounting for all of these horizons. In a preferred embodiment, an overall SRI value is determined by normalizing all four of these horizon values in order to account for potential error that exists amongst model predictions as the model prediction horizon increases. In some embodiments, the normalizing comprises calculating a mean of these four values.

One Example Embodiment of Systems to Support Medical Therapy Decisions:

Systems to support medical therapy decisions generally comprises a non-transitory computer readable medium having a computer readable program code embodied therein, said computer readable program code configured to be executed to implement the method described herein. In some embodiments, the systems include modules to provide the following: 1) a determination of a risk index of a patent given current and predicted patient data, 2) a determination of a directive recommendation to address the risk index, 3) data visualization and system interaction through a user interface (UI), and 4) data storage/maintenance.

Figure 9:
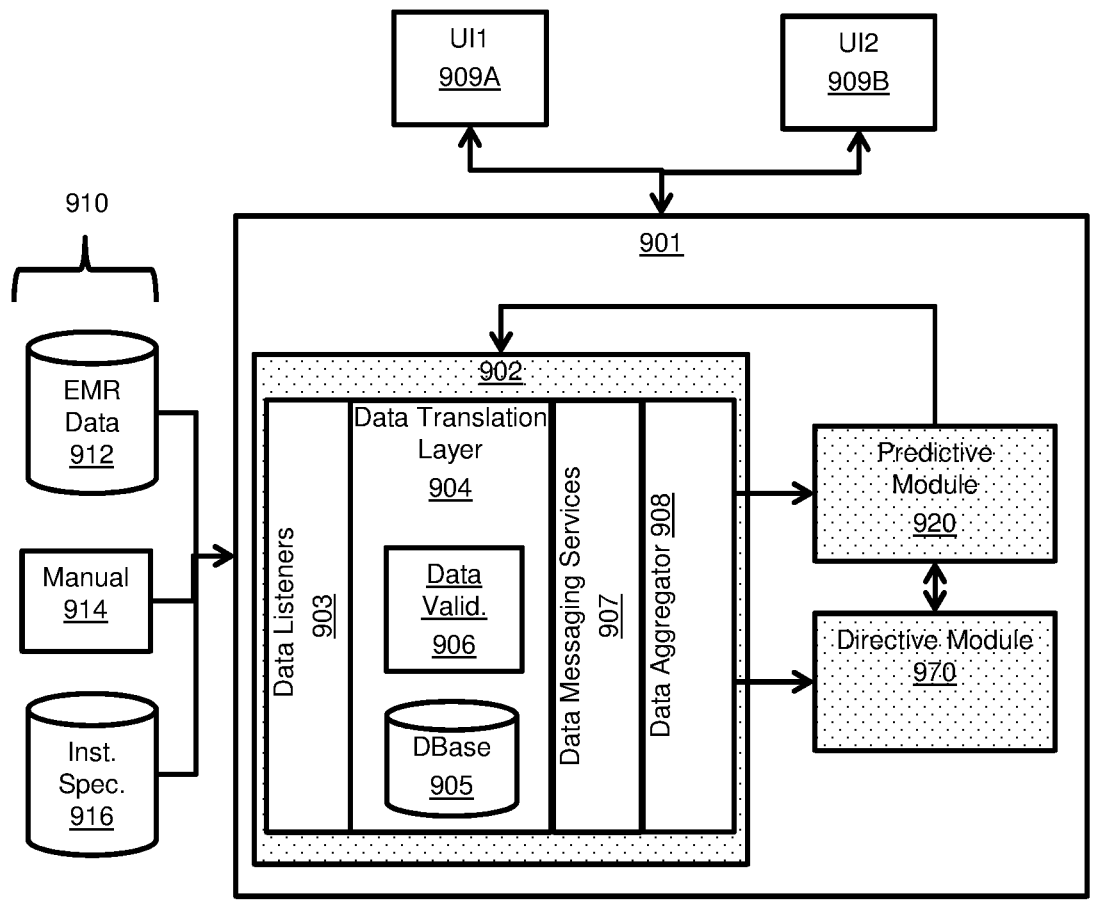
FIG. 9 illustrates one example embodiment of a processor-based system suitable for a system to support medical therapy decisions.

FIG. 9 illustrates one example embodiment of a system to support medical therapy decisions consistent with the methods described in FIGS. 1A and 1B above. System 900 comprises data sources 910, a processor based system 901 and user interfaces 909A and 909B. The data sources 910 may be EMR data 912, manually entered data 914 or institution specific sources 916.

The processor-based system 901 includes a software framework configured to provide data listeners 903, a data translation layer 904, data messaging services 907 and a data aggregator 908. The data listeners 903 receive data from the data sources 910 and transfer the data to the data translation layer 904. In some embodiments, the data is received in an EMR-specific format (e.g. HL7 for civilian healthcare). The data translation layer 904 is designed as an adaptable interface for the various data sources 901. The data translation layer 904 takes the data in the format received from the data listeners 903 and translates it to a generic object model that will provide a domain agnostic representation of the data coming into the software framework.

The processor-based system 901 provides input to the preventive antibiotic therapy recommendation module 920 and the directive antibiotic therapy recommendation module 970.

The preventive antibiotic therapy recommendation module 920 provides the functionality to determine predictive therapy data. This module 920 generally comprises: neural network models to predict EMR data sources used as diagnostic criteria for sepsis, a Sepsis Risk Index algorithm, algorithm-generated alerts to notify healthcare providers to perform actions such as order a set of cultures and consider initiation of broad spectrum antibiotic therapy. Overall the models/algorithms in this module 920 are configured to support timely initiation of preventive antibiotic therapy when an infection is present or probable in the future. These therapies may contribute to improved patient outcomes such as reduction of mortality and ICU/hospital length of stay. This module may work cooperatively with the directive antibiotic therapy recommendation module 970.

The preventive antibiotic therapy recommendation module 920 includes the Sepsis Risk Index algorithm. Inputs to the SRI algorithm are the result of the neural network models predicating trajectories input variables relating to the patient's current state. These variables may comprise data types such as Heart Rate, Respiration Rate, Systolic Blood Pressure, Mean Arterial Pressure, Temperature, Urine Output, Blood Glucose, White Blood Cell Count, Creatinine, Platelet Count, and Lactate. These predicted and current values are compared to thresholds associated with Sepsis and then combined to derive the Sepsis Risk Index.

The directive antibiotic therapy recommendation module 970 provides supplementary decision support for making medical therapy decisions. This module 970 generally comprises the SOFMs/Kohonen neural networks and receives input data used in the preventive antibiotic therapy recommendation module 920 as well as other data such as the specific antibiotic prescribe, its dose and cost from the database 905. With a large input of data the SOFMs are able to learn and recognize clusters in the data when new data is presented.

In operation, the SOFM based directive model initially populates a list of potential antibiotics that are rank-ordered via rule-based logic and algorithms based on knowledge of key underlying system data sources. The directive model inputs representing directive antibiotic treatment decisions are then varied iteratively in order to identify the most appropriate directive antibiotic therapy intervention leading to the most favorable set of patient outcomes.

A database 905 is used to store relevant patient EMR data and institution-specific data (e.g. antibiograms, antibiotic cost information, etc.), as well as results from the predictive models and algorithms. This includes integrated data that was parsed from the USAISR dataset into this database. Access to the data structured within this database 905 supports the system's functionality including simulated real-time playback of patient data (on a patient by patient basis), as well as retrospective analysis of an entire patient record, or segment of a record.

The user interfaces 909A and 909B may be any type of user interface (UI) suitable to present system data and alarms to a user. To provide the data visualization and system interaction capabilities, a visualization subsystem retrieves necessary data from a database 905 and displays it within the main UI. In some embodiments, the user interface is integrated into a UI similar to that disclosed in U.S. Pat. Pub. No. 2015/0227710, published on Aug. 13, 2015, the entire contents of which are herein incorporated by reference.

Figure 2:
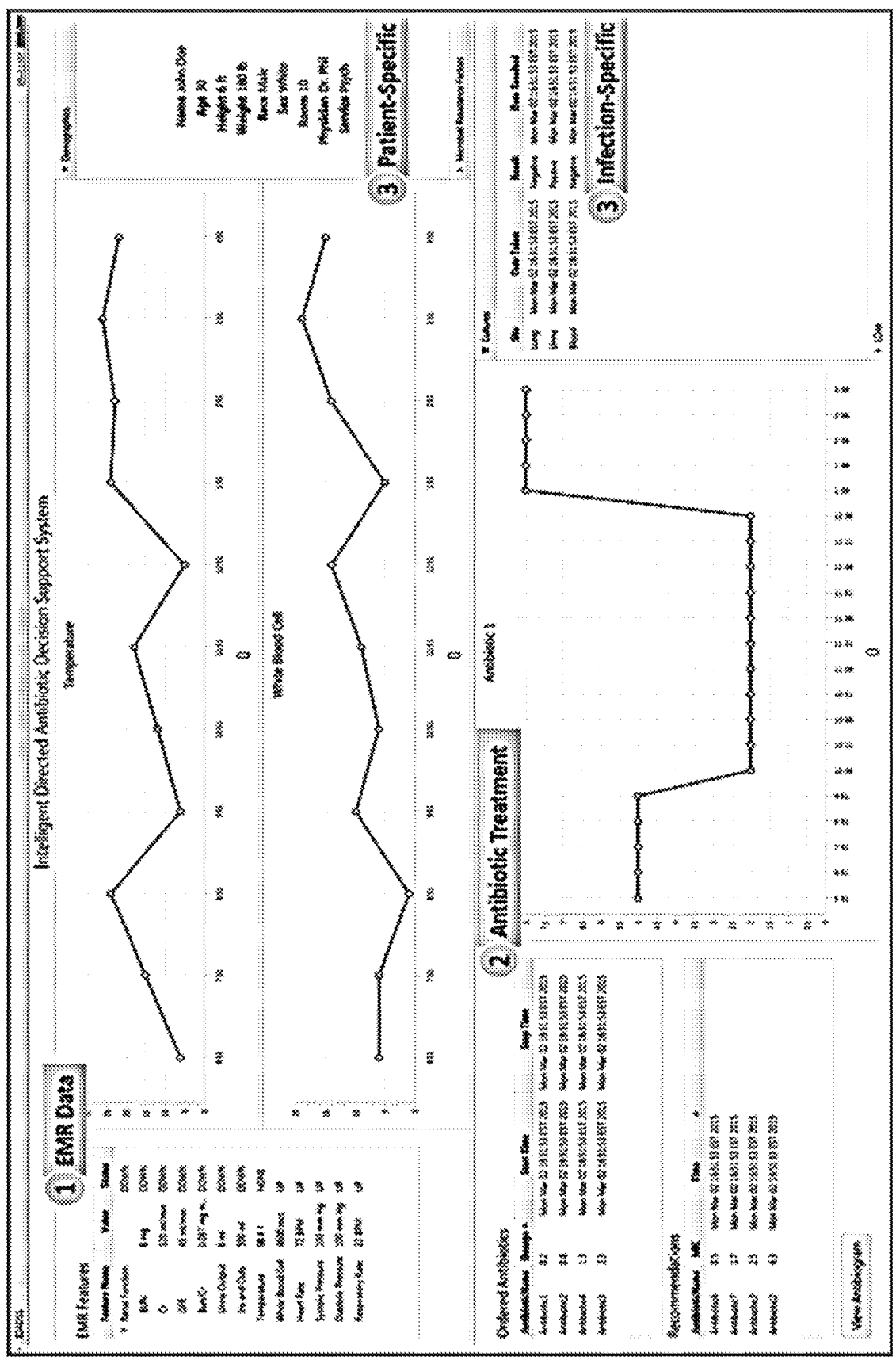
FIG. 2 illustrates an example embodiment of a user interface.

One example embodiment of a UI is shown in FIG. 2. Overall, the UI is designed to provide functionality, features, and access to data within a single unified platform. Three requirements may be accommodated for by: 1) configurable plots of relevant EMR data sources, 2) historical antibiotic delivery overview and system recommendations, and 3) additional data sources to provide more context and supporting information to guide antibiotic treatment.

In support of the first requirement, the UI is designed to plot multiple EMR data sources simultaneously. To maximize utility of this feature, a comprehensive list of EMR data sources is present within the UI. The UI is designed such that a user can select any of the EMR data sources and plot available data. This feature allows users to easily view multiple combinations of EMR data sources with respect to current and historical antibiotic therapy.

In order to support the second requirement, a configurable plot for current and historical antibiotic treatment, as well as system-generated recommendations was included. A user selects from a list of antibiotics present within a table on the main visualization to plot historical dosing of a specific ordered antibiotic (e.g. vancomycin peaks and troughs). System-generated antibiotic dosing recommendations are also included in a similar table below the ordered antibiotics. Users can also choose to plot ordered antibiotics versus system recommendations to evaluate if their chosen antibiotic regimen aligns with system-generated recommendations. Additionally, to help guide appropriate treatment, a user can view the antibiogram associated with a specific unit. Lastly, users have the ability to display the laboratory culture results throughout a patient's length of stay. The system-generated alerts will be executed which support identification of an infection source (i.e. microorganism) and its site (e.g. lung, blood, urine, etc.). This is helpful as it will provide further context into origin of infection and help to further target and focus therapy.

To support the third requirement, additional relevant data sources are displayed within the main UI. These data sources fall into two categories: (1) patient-specific factors and (2) infection-specific factors. Patient-specific factors represented within the main UI include patient demographics, and patient-specific microbial resistance factors. Patient demographics include key information such as but not limited to: weight, height, age, and allergies to medications. Patient-specific microbial resistance factors include but are not limited to: number of days in the hospital, transfers from hospital units or other internal or external facilities, diagnosis of diabetes mellitus, whether the patient is on dialysis, recent surgeries and hospitalizations within the past 90 days, and previous antibiotic utilization over the past 90 days. In addition to patient-specific factors, infection-specific factors are also represented within the UI. These factors include laboratory culture results as well as lines, tubes, and drains (LDAs). Laboratory culture results include information such as the date, time, culture site, and results of each culture. Lines, tubes, and drains will be identified based on their insertion/removal dates and times such that they can be associated with incidence of infection.

Embodiments of the UI may also include the following functionality:

a) view multiple relevant EMR data streams (e.g. heart rate, temperature, etc.) simultaneously in the context of antibiotic therapy;

b) visualize results of predictive models designed to forecast changes in specific EMR data and support derivation of a novel SRI;

c) alert system users when to consider starting broad spectrum antibiotic therapy based on the Sepsis Risk Index, and identify current/historical instances of antibiotic therapy;

d) visualize historical patient data (for a complete patient record), or simulate real-time patient data via iterating through hour by hour EMR updates; and e) access to an institution's antibiogram for a particular hospital unit from within application.

Figure 3A:
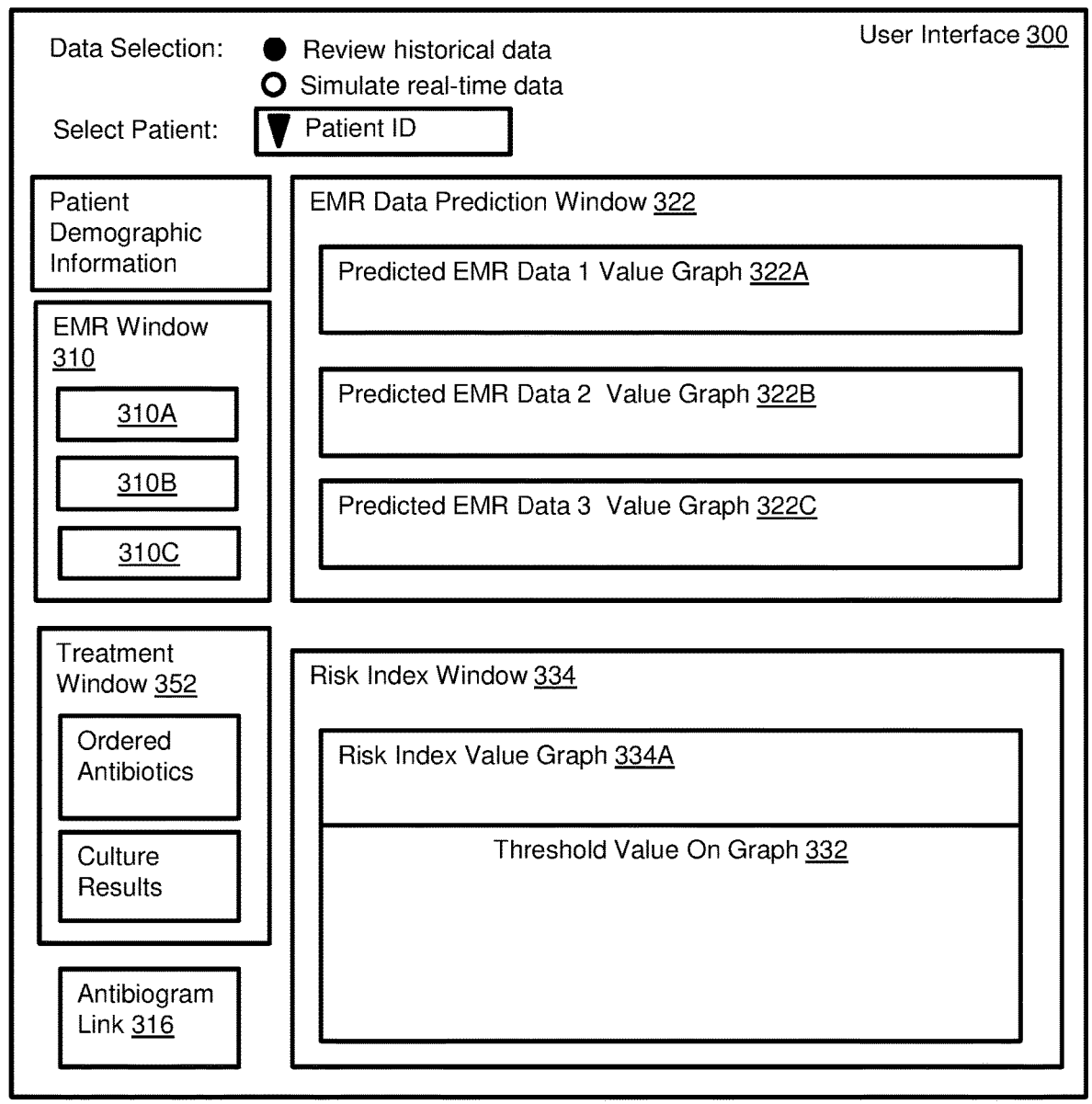
FIGS. 3A and 3B illustrate example embodiments of a user interface.
Figure 3B:
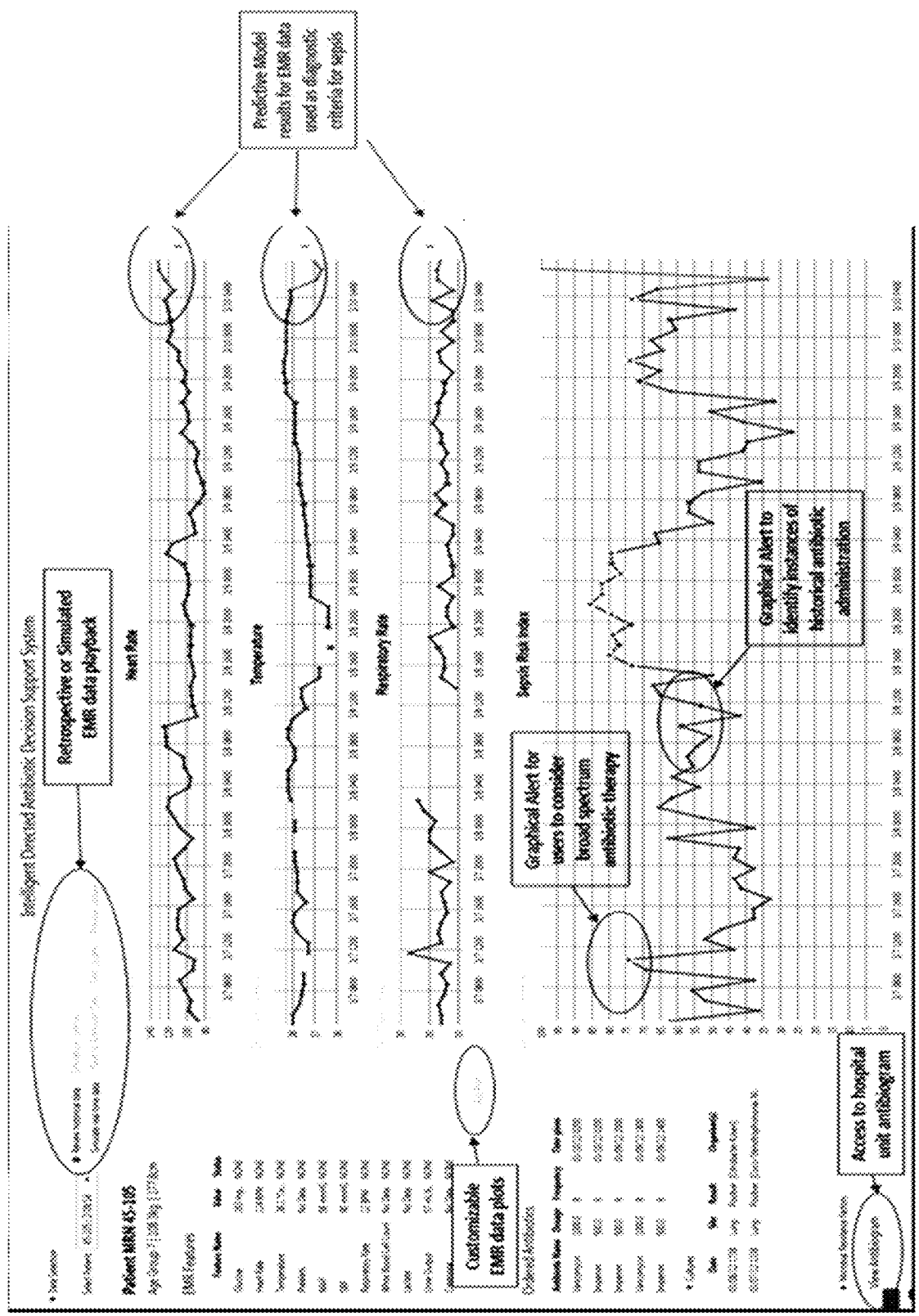

An example embodiment of the UI, along with a breakdown of the system features and functionality incorporated into one embodiment of the system is shown in FIGS. 3A and 3B. As shown in FIG. 3A, the user interface 300 comprises an electronic medical record (EMR) window 310 configured to display EMR data values of available EMR data sources for the patient (here types 310A, 310B an 310C), a data prediction window 322 configured to display predicted EMR data values of the patient (here plot graphs 322A, 322B and 322C), a risk index window 334 configured to display a risk index value (here as a graph 334A) and an access interface 316 configured to provide access to an antibiogram of the health care facility. The risk index window 334 may also display the threshold value of the risk index on the graph at 332. FIG. 3B shows a similar embodiment of FIG. 3A with some of the data populated. The user interface may also provide the ability for the user to select whether the interface will be used to review historical data or to simulate real-time data.

In some embodiments, the UI may also include a range of alerts that provide prompts to perform tasks in a timely manner, such as prompting users to assess for de-escalation of antibiotic therapy or alerts to indicate blood draws are required. Additionally, the UI may include enhanced system alerts (e.g. SRI alert to identify when to consider initiating broad spectrum antibiotic therapy) to align with and improve the overall treatment provided by the medical team. This includes different types of alerting mechanisms such as visual (e.g. pop-up windows) and auditory (i.e. audible alerts). Other embodiments may include improving EMR data graphs to better adapt scaling/resolution based on new incoming data, and to include legends which support better identification of plot contents.

As will be readily apparent to those skilled in the art, systems and methods to support medical therapy decisions can be embodied in hardware, software, or a combination of hardware and software. For example, a computer system or server system, or other computer implemented apparatus combining hardware and software adapted for carrying out the methods described herein, may be suitable. One embodiment of a combination of hardware and software could be a general purpose computer system with a computer program that, when loaded and executed, carries out the respective methods described herein. In some embodiments, a specific use computer, containing specialized hardware for carrying out one or more of the instructions of the computer program, may be utilized. In some embodiments, the computer system may comprise a device such as, but not limited to a digital phone, cellular phone, laptop computer, desktop computer, digital assistant, server or server/client system.

Computer program, software program, program, software or program code in the present context mean any expression, in any language, code or notation, of a set of instructions readable by a processor or computer system, intended to cause a system having an information processing capability to perform a particular function or bring about a certain result either directly or after either or both of the following: (a) conversion to another language, code or notation; and (b) reproduction in a different material form. A computer program can be written in any form of programming language, including compiled or interpreted languages, and it can be deployed in any form, including as a stand-alone program or as a module, component, subroutine, or other unit suitable for use in a computing environment.

Figure 10:
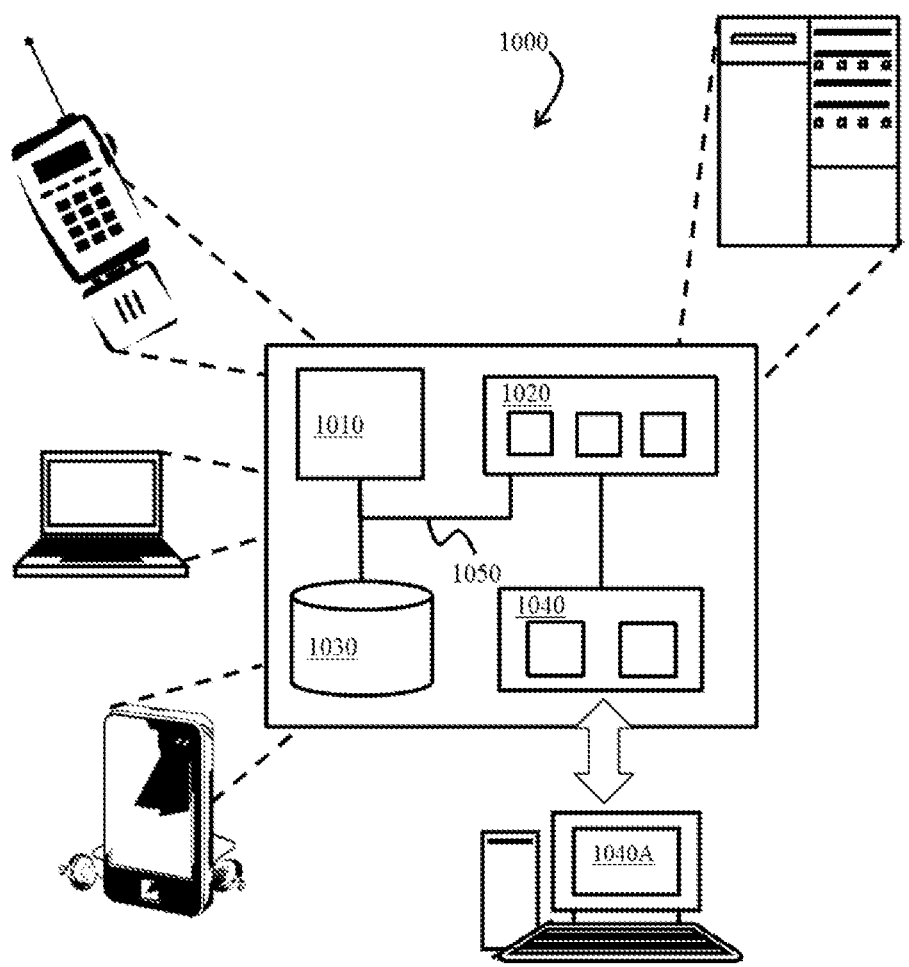
FIG. 10 illustrates one example embodiment of a computer system suitable for a system to support medical therapy decisions.

FIG. 10 is a schematic diagram of one embodiment of a computer system 1000 by which the environmental system reaction methods may be carried out. The computer system 1000 can be used for the operations described in association with any of the computer implemented methods described herein. The computer system 1000 includes at least one processor 1010, a memory 1020 and an input/output device 1040. Each of the components 1010, 1020, and 1040 are operably coupled or interconnected using a system bus 1050. The computer system 1000 may further comprise a storage device 1030 operably coupled or interconnected with the system bus 1050.

The processor 1010 is capable of receiving the instructions and/or data and processing the instructions of a computer program for execution within the computer system 1000. In some embodiments, the processor 1010 is a singlethreaded processor. In some embodiments, the processor 1010 is a multi-threaded processor. The processor 1010 is capable of processing instructions of a computer stored in the memory 1020 or on the storage device 1030 to communicate information to the input/output device 1040. Suitable processors for the execution of the computer program instruction include, by way of example, both general and special purpose microprocessors, and a sole processor or one of multiple processors of any kind of computer.

The memory 1020 stores information within the computer system 1000. Memory 1020 may comprise a magnetic disk such as an internal hard disk or removable disk; a magneto-optical disk; an optical disk; or a semiconductor memory device such as PROM, EPROM, EEPROM or a flash memory device. In some embodiments, the memory 1020 comprises a transitory or non-transitory computer readable medium. In some embodiments, the memory 1020 is a volatile memory unit. In another embodiments, the memory 1020 is a non-volatile memory unit.

The processor 1010 and the memory 1020 can be supplemented by, or incorporated in, ASICs (application-specific integrated circuits).

The storage device 1030 may be capable of providing mass storage for the system 1000. In various embodiments, the storage device 1030 may be, for example only and not for limitation, a computer readable medium such as a floppy disk, a hard disk, an optical disk, a tape device, CD-ROM and DVD-ROM disks, alone or with a device to read the computer readable medium, or any other means known to the skilled artisan for providing the computer program to the computer system for execution thereby. In some embodiments, the storage device 1030 comprises a transitory or non-transitory computer readable medium.

In some embodiments, the memory 1020 and/or the storage device 1030 may be located on a remote system such as a server system, coupled to the processor 1010 via a network interface, such as an Ethernet interface.

The input/output device 1040 provides input/output operations for the system 1000 and may be in communication with a user interface 1040A as shown. In one embodiment, the input/output device 1040 includes a keyboard and/or pointing device. In some embodiments, the input/output device 1040 includes a display unit for displaying graphical user interfaces or the input/output device 1040 may comprise a touchscreen. In some embodiments, the user interface 1040A comprises devices such as, but not limited to a keyboard, pointing device, display device or a touchscreen that provides a user with the ability to communicate with the input/output device 1040.

The computer system 1000 can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, wireless phone networks and the computers and networks forming the Internet.

Figure 11:
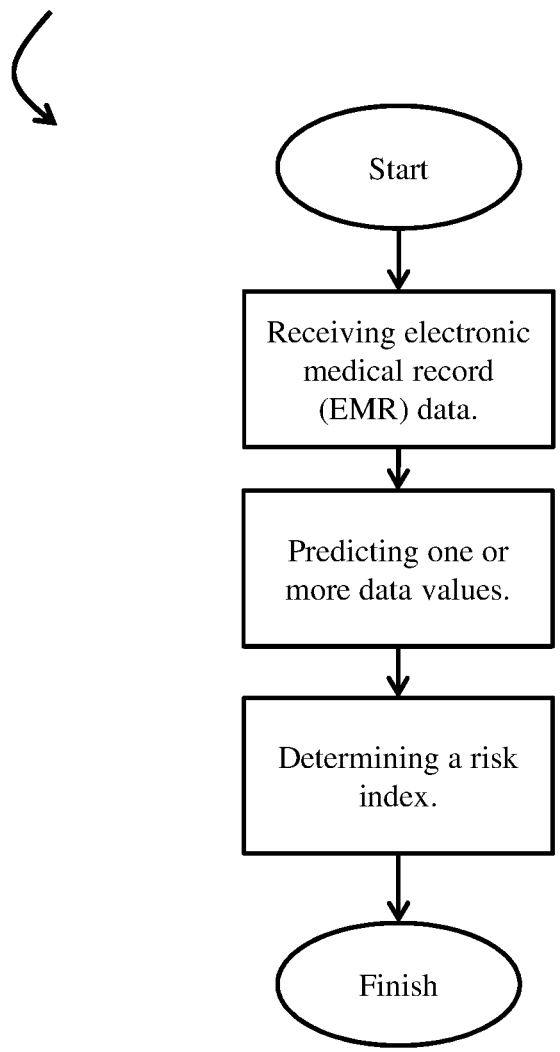
FIG. 11 illustrates one example embodiment of methods to support medical therapy decisions.

In some embodiments, the methods to support medical therapy decisions may be performed through the execution of computer program code programmed to implement these methods. A functional diagram of an example embodiment of these methods is shown at FIG. 11. As shown, the method 1100 comprises receiving electronic medical record (EMR) data and predicting one or more data values from the EMR data. In some embodiments, as shown, the method further comprises determining a risk index from the predicted data values. Other embodiments of the methods disclosed herein may also be performed through execution of computer program code.

Figure 12:
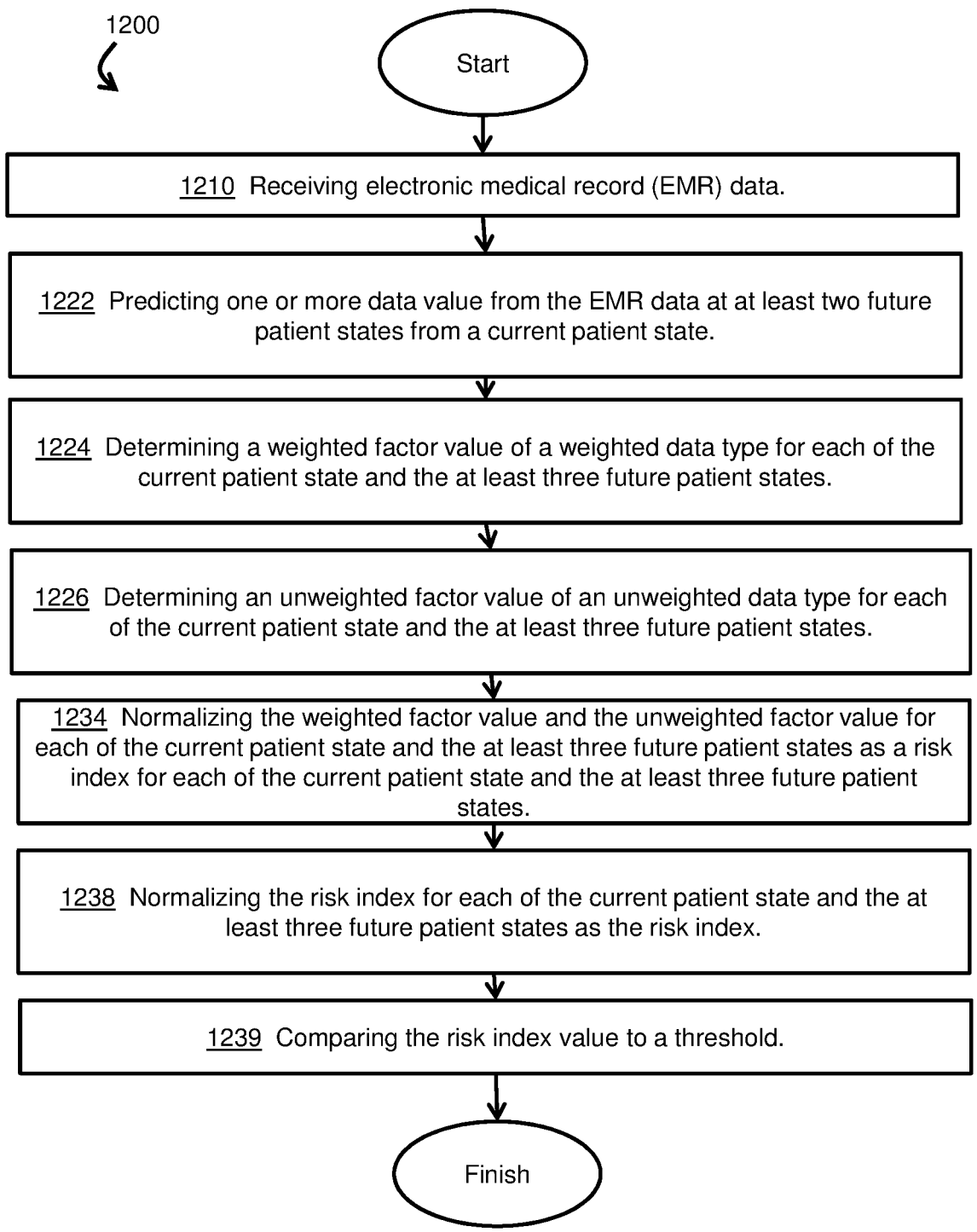
FIG. 12 illustrates one example embodiment of methods to support medical therapy decisions.

FIG. 12 illustrates one example embodiment of methods to support medical therapy decisions. As shown, step 1210 comprises receiving electronic medical record (EMR) data. Step 1222 comprises predicting one or more data value from the EMR data at at least two future patient states from a current patient state. Step 1224 comprises determining a weighted factor value of a weighted data type for each of the current patient state and the at least three future patient states. Step 1226 comprises determining an unweighted factor value of an unweighted data type for each of the current patient state and the at least three future patient states. Step 1234 comprises normalizing the weighted factor value and the unweighted factor value for each of the current patient state and the at least three future patient states as a risk index for each of the current patient state and the at least three future patient states. Step 1238 comprises normalizing the risk index for each of the current patient state and the at least three future patient states as the risk index. Step 1239 comprises comparing the risk index value to a threshold.

One example embodiment of the systems and methods to support medical therapy decisions may be embodied in a computer program product, the computer program product comprising a computer readable medium having a computer readable program code tangibly embodied therewith, the computer program code configured to implement the methods described herein, and which, when loaded in a computer system comprising a processor, is able to carry out these methods.

One Example Embodiment of the System in Operation:

In an example embodiment addressing sepsis risk, the predictive models: (1) provided prediction of key EMR data sources which are diagnostic criteria for sepsis, and (2) derived a 0-100 Sepsis Risk Index, which represents the "risk" for a patient to acquire sepsis based on real-time and predicted EMR data. In this embodiment, algorithms and models were generated using a dataset obtained from USAISR.

Development and evaluation of one embodiment of determining SRI values was based on a dataset of 17 patients admitted to the Burn ICU at San Antonio Military Medical Center (SAMMC) obtained from United States Army Institute of Surgical Research (USAIR). The dataset provided by USAISR consisted of EMR data collected in burn patients 72 hours prior to a diagnosis of sepsis. This data was parsed to yield a numerical dataset for model/algorithm development. Through an examination of eleven patient specific electronic medical record data sources used to derive the Sepsis Risk Index it was evident that data sources were asynchronously updated within an EMR system. Because of the asynchronous nature of the data the SRI only relies on data when it is available. Checks are made when computing the each time horizon SRI to ensure data is available for Heart Rate, Respiration Rate, Systolic Blood Pressure, Mean Arterial Pressure, Temperature, Urine Output, Blood Glucose, White Blood Cell Count, Creatinine, Platelet Count, and Lactate. If this data is unavailable at the current time, they will be excluded from the SRI for the four time horizons.

To support the predictive models and analytics, an application was developed to parse and convert the dataset provided by USAISR to a numerical format. The numerical dataset generated was used to train time-delay neural networks for prediction of EMR data points. This application was used to translate the functionality of the developed time-delay neural network models to a Java-based system. As such a C++ dynamic-link library was generated which provided the desired neural network model functionality. A model service was developed in Java which utilizes the Java Native Interface (JNI) to provide access to EMR and patient-specific data (collocated in a local database) and C++ neural network model functionality.

Neural network models were used to predict EMR data sources as diagnostic criteria for sepsis. These prediction models were developed for relevant data changes using a prediction horizon of 3 hours. The developed models are thus designed to predict future trends/changes in EMR data at 1, 2, and 3 hours from a current real-time patient state (where state comprises all current real-time EMR and patient-specific data sources). The predictive models were built as time-delay neural network models which utilize a history of EMR/patient-specific data as well as current data to generate predictions. The initial developed models were designed to account for a history of 3 hours of EMR data vectors. Specific EMR data sources which were used as inputs to these preliminary predictive models included: steroids, fluids, vasoactive agents, EMR data surrounding glycemic control (i.e. blood glucose values, insulin delivered), arterial blood gas results, chem panel (laboratory results), platelet count, white blood cell count, lactate, temperature, heart rate, respiratory rate, systolic blood pressure, mean arterial pressure, and urine output. Multiple predictive models were developed for the vital signs (commonly used as diagnostic criteria for sepsis) which were frequently documented in the dataset provided by AISR. Predictive models were also developed for the following vital signs: (1) heart rate, (2) respiration rate, (3) temperature, (4) blood pressure, (5) mean arterial pressure, and (6) urine output.

From all of these potential data sources, it was determined that the EMR data sources to serve as the best diagnostic criteria for sepsis were: heart rate, respiration rate, systolic blood pressure, mean arterial pressure, temperature, urine output, blood glucose, white blood cell count, creatinine, platelet count, and lactate.

Figure 4:
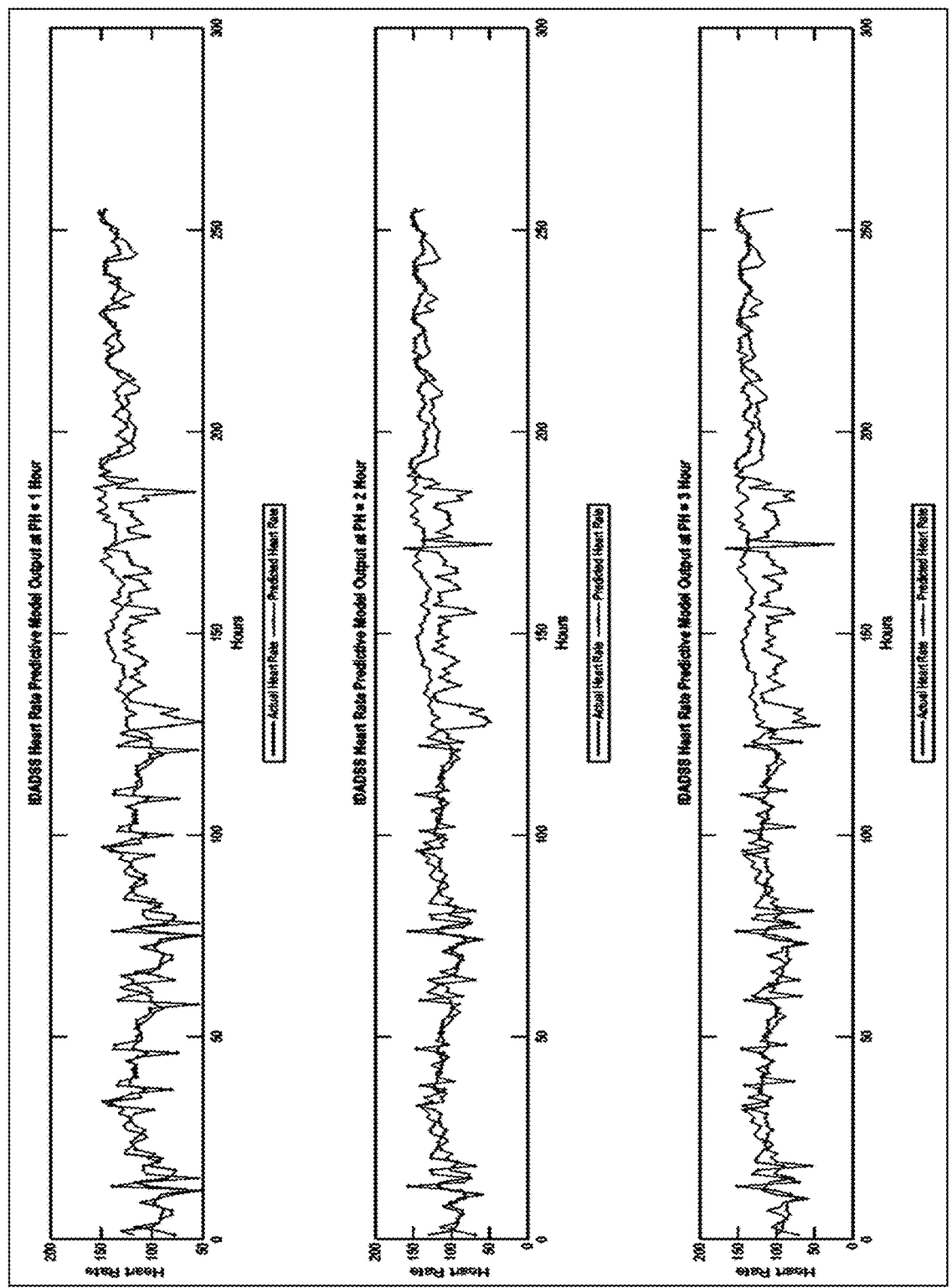
FIG. 4 shows example predictive model results for heart rate evaluated across four patients to simulate real-world model performance in the clinical setting.

In order to evaluate the predictive model performance on unseen patient data and to effectively simulate real-world performance within the clinical setting, four models were developed leaving data from a single patient out of the model training set. FIG. 4 demonstrates predictive model performance (for a heart rate predictive model) across four patients dataset using >250 hours of EMR data from the USAISR. As anticipated model error increased when predicting heart rate values across the 3 hour model prediction horizon. Overall model error, expressed as mean absolute difference percent (MAD %), was calculated as 11.74%, 14.84%, and 16.08% at 1, 2, and 3 hour predictions across the patient data used for model validation. Given the performance of predictive models performed as expected, an overall SRI value for each of these same four patients was then calculated. Using an initial estimated threshold of 70 for cutoff of the SRI, these patients would have received antibiotic therapy intervention earlier when compared to when they received antibiotics based on their medical records.

Once the predicted data values are determined with the predictive models, the values are compared to predetermined thresholds. The eleven EMR data sources and corresponding thresholds which are currently used to calculate the SRI values are shown in FIG. 6B and the SRI threshold defined for alerting system users to consider initiation of broad spectrum antibiotic therapy is notionally set to 70, however, other thresholds may be defined based on statistical analysis and algorithm performance (i.e. sensitivity/specificity of alerts) from larger patient populations.

Figure 5:
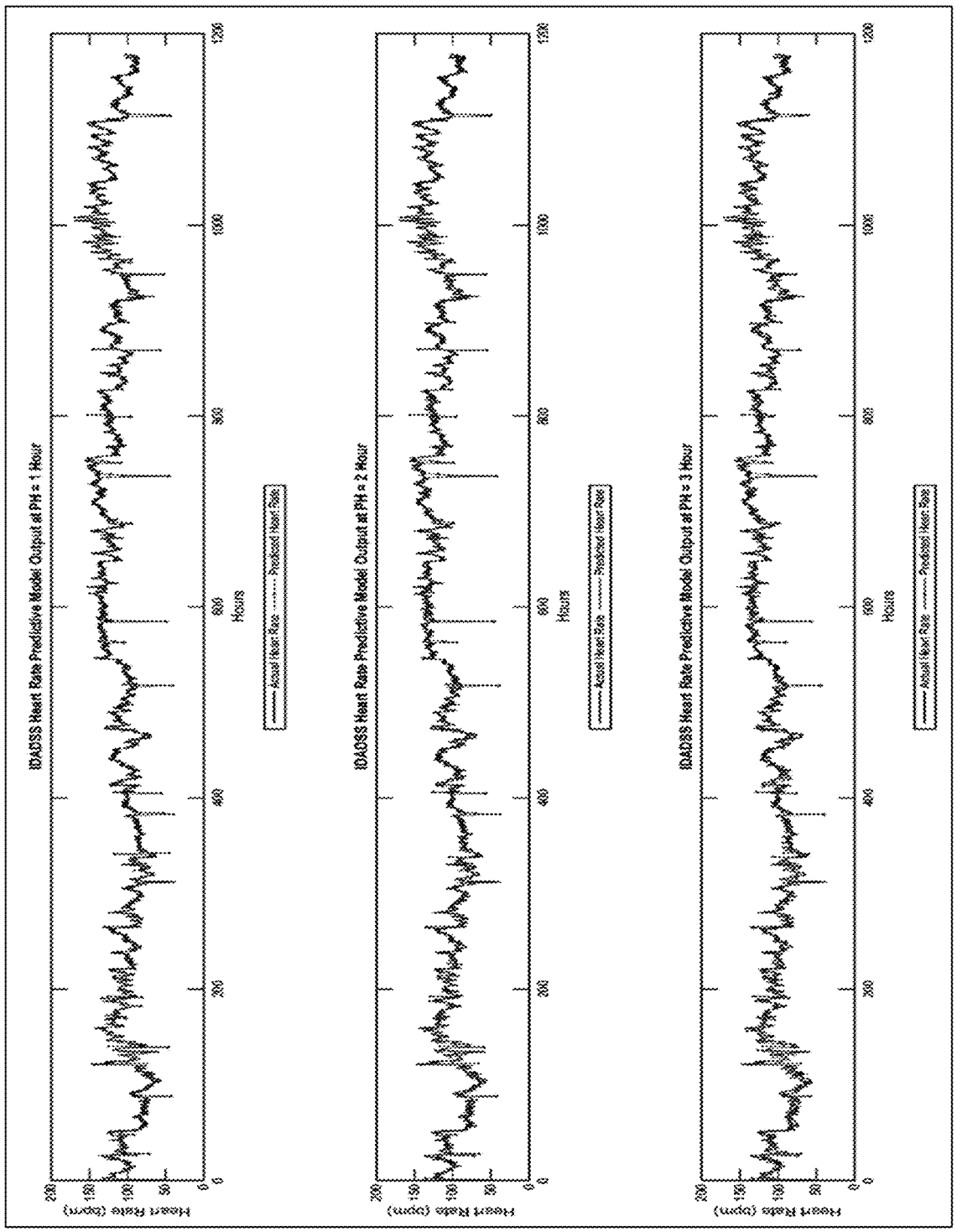
FIG. 5 shows example predictive model results for heart rate evaluated across the entire USAISR dataset to demonstrate overall neural network "model fit"

FIG. 5 contains model predictions generated by the neural network when applied to the model training set, and demonstrates the overall neural network "model fit" to the USAISR dataset when predicting heart rate. Model predictions included in both FIGS. 4 and 5 track changes in heart rate across the model prediction well, with the overall "model fit" shown in FIG. 5 being considerably more accurate. This is expected as neural network and other machine learning-based models are designed to discover complex non-linear patterns and relationships in data. It is anticipated that model performance increases significantly when model training set size increases.

Figure 7:
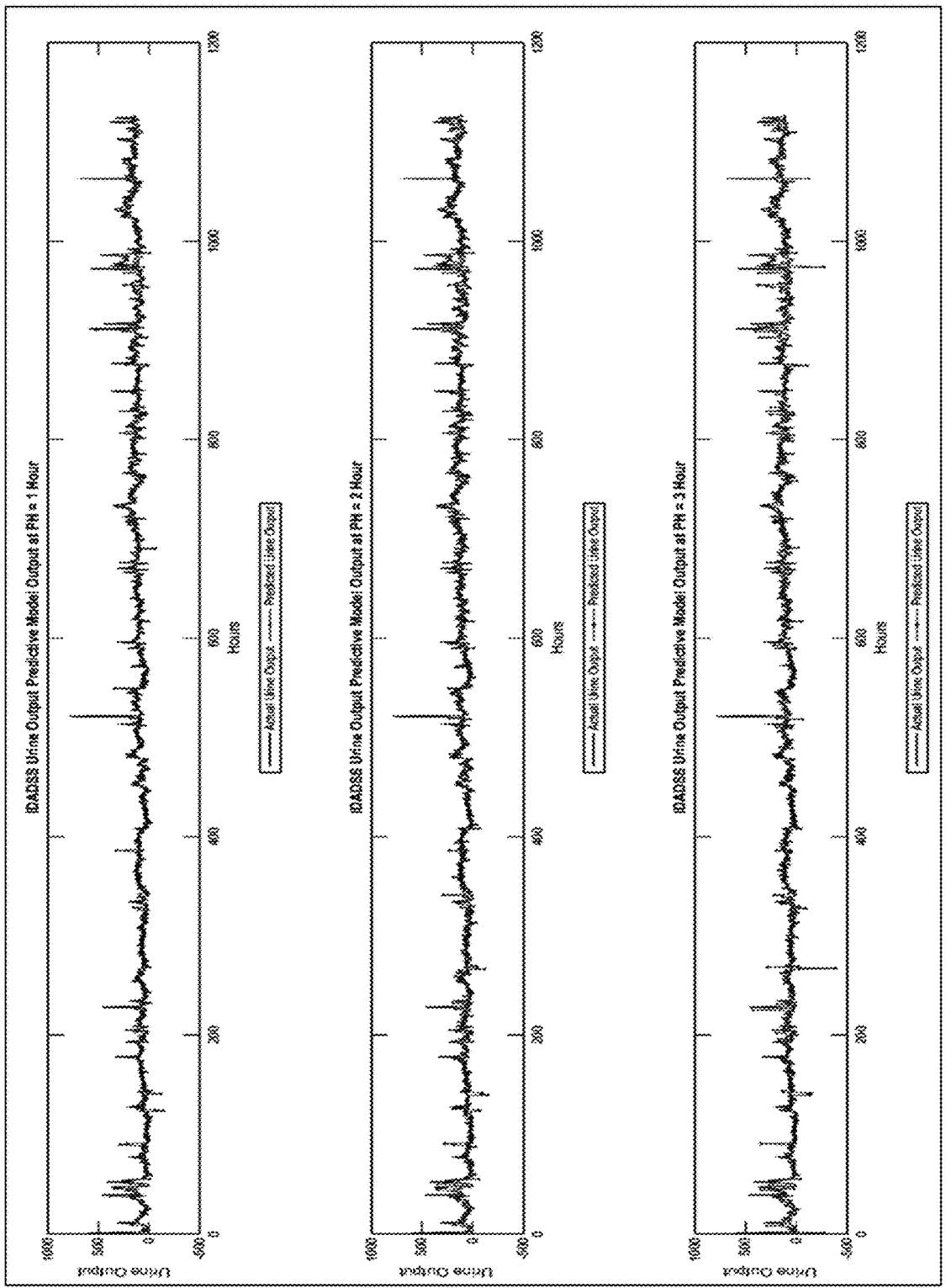
FIG. 7 shows example predictive model results for urine output evaluated across the entire USAISR dataset.

FIG. 6A shows the overall model error (expressed as MAD %) in terms of the overall model fit when applied to the comprehensive USAISR dataset for each vital sign and sepsis criterion of interest, as well as the leave-one-out validation results of the heart rate predictor model. It should be noted that the predictive model for urine output performs the poorest amongst all of the models and this is attributed to the underlying model training data. There are sudden and significant increases in urine output which occur throughout the dataset and predictability of these "spikes" is poor. Overall, the model tracks trends and changes in urine output well, but performs poorly during these instances. This contributes to the large error in model predictions as shown in FIG. 6A. FIG. 7 demonstrates model predictions generated by the urine output model when applied to the model training set to demonstrate overall model fit.

Upon receipt of new EMR data, four sepsis risk indices are calculated representing 1) real-time sepsis risk, 2) sepsis risk at t+1 (hour), 3) sepsis risk at t+2 (hours), and 3) sepsis risk at t+3 (hours). The overall SRI (derived for UI plot as shown in FIGS. 3B, 7 and 8) is then calculated as the mean of these four values. We have chosen to implement the mean of these four values in order to account for potential error that exists amongst model predictions as the model prediction horizon increases.

The resulting SRI value is then used to identify when a user of the system should consider initiation of broad spectrum antibiotic therapy. During initial implementations, an initial SRI threshold value of 70 was used. Once this threshold was met, graphical alerts were presented on the main UI of the system along with instances where antibiotics administration occurred.

Figure 8A:
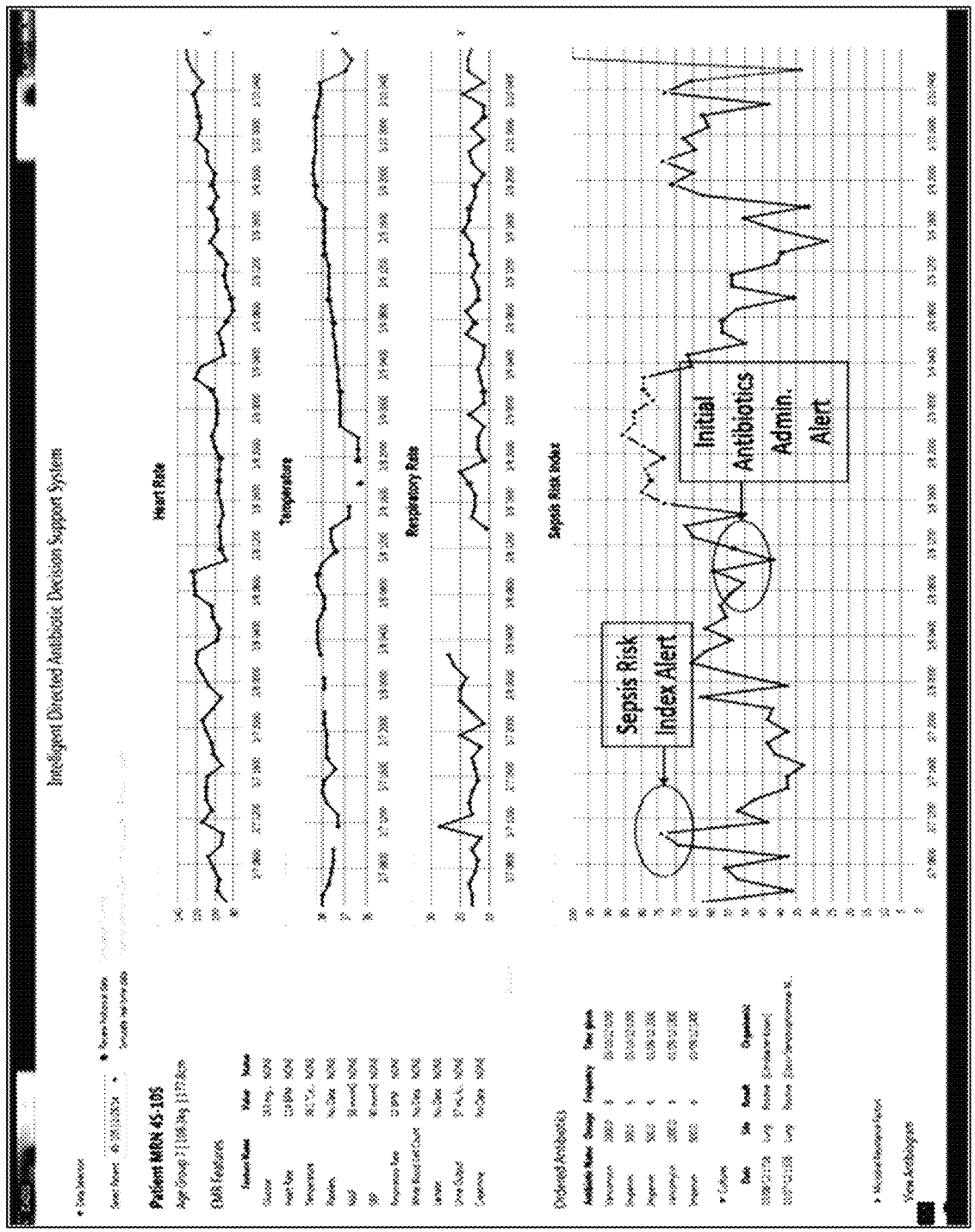
FIG. 8A shows example Sepsis Risk Index and antibiotics administration alerts generated for patient 45-105 of USAISR dataset.
Figure 8B:
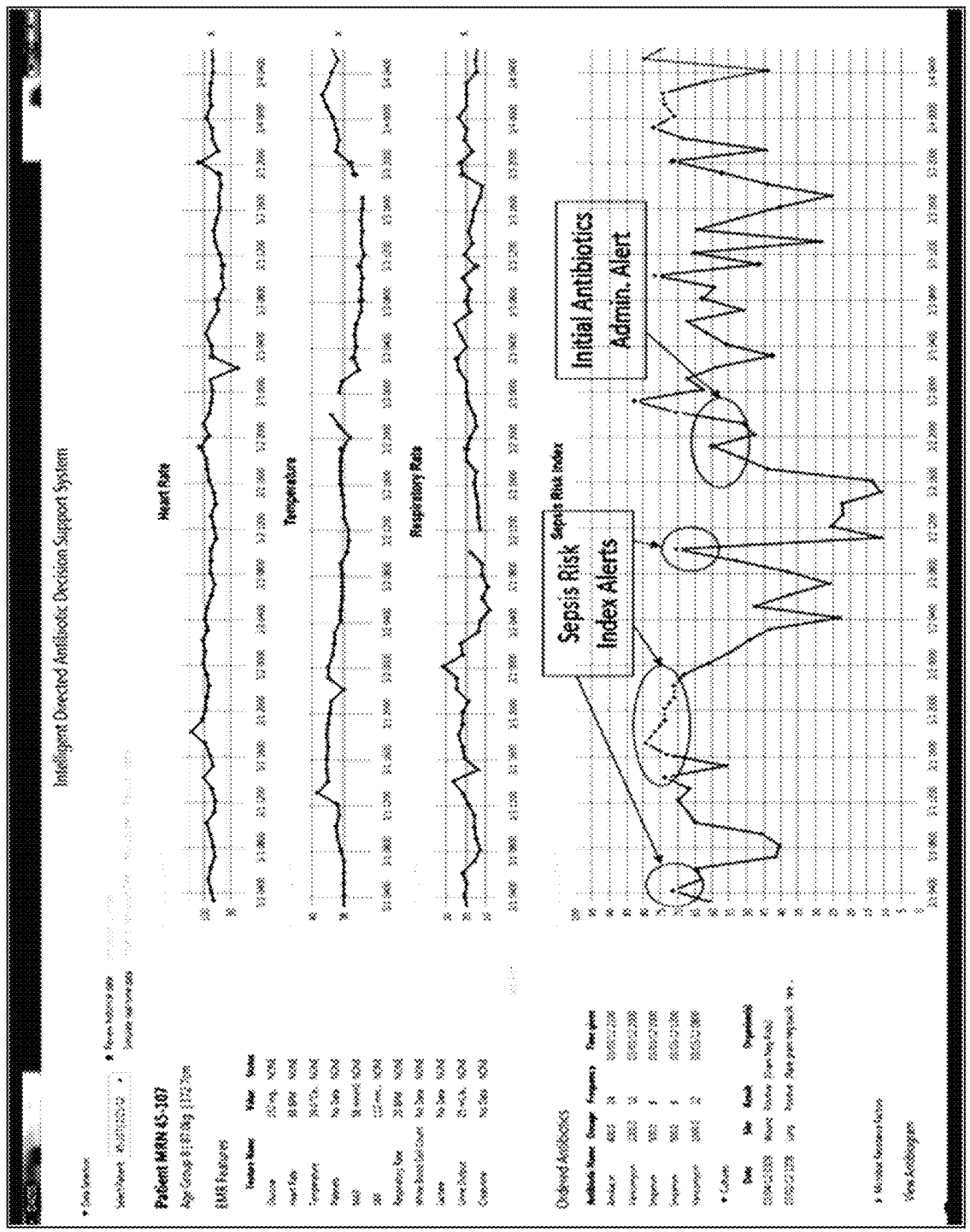
FIG. 8B shows example Sepsis Risk Index and antibiotics administration alerts generated by for patient 45-107 of USAISR dataset.

FIGS. 8A and 8B show annotated system UIs for two patients (45-105 and 45-107) where Sepsis Risk Index exceeded the predefined threshold and alerts are indicated by red circles. Also shown are alerts for when antibiotics were given by healthcare staff as indicated by the green circles. A visual inspection indicates that if antibiotic delivery was started when the generated SRI values exceeded the predefined threshold it would have resulted in antibiotics being delivered much sooner than what actually occurred in practice. Based on previous research available, initiating broad spectrum antibiotic therapy at these times may have resulted in more favorable outcomes by avoiding potentially significant delays in antibiotics administration. As can be seen in FIGS. 8A and 8B, in both cases SRI alerts (to consider initiation of broad spectrum antibiotic therapy) occurred >24 hour before actual antibiotic therapy was started.

The results of using this embodiment with the dataset provided were positive. There was a 41.7% mortality rate amongst patients evaluated within the USAISR dataset (i.e. 5 of 12 patients died). Across 80% of the patients who died, the methods and Sepsis Risk Index alerted to need of antibiotics administration before they were actually delivered in practice. The system generated Sepsis Risk Index alerts were generated an average of 7.75 hours before antibiotics were delivered as documented in a patient's electronic health record. This is a potentially important finding as the system will be able to alert users (i.e. healthcare providers) to initiate antibiotics therapy sooner which may potentially contribute to a reduction of mortality, and lengths of stay in the ICU and hospital based on the existing literature.

Alternative Embodiments of Systems and Methods to Support Medical Therapy Decisions:

Other embodiments of the system and methods to support medical therapy decision may include addition features.

In some embodiments, as shown in FIG. 9, some components of the software architecture (predictive module, directive modules and UIs) will not communicate directly with the EMR, but rather through a service that will provide a layer of security between the two systems and mitigate or prevent data consistency issues. EMR data will be acquired by the data translation layer (DTL) 904 which is designed as an adaptable interface for various data sources 910. This will be accomplished by receiving the data 910 in an EMR-specific format (e.g. HL7 for civilian healthcare institutions, and applicable future DoD EMR standards) and converting it to a generic object model which will provide a source agnostic representation of the data being used by the software framework 902. The generic object model in the DTL 904 will provide a common ontology that will be used to support analysis, processing, storage, and visualization of the collected healthcare data.

In some embodiments, the systems will exist as an individual decision support system (DSS) module that will have access to healthcare data within the architecture introduced in FIG. 9. This feature will make integration of additional DSS modules flexible and prevent them from having to re-develop connections to different healthcare institutions' data sources. Output from all modules within the architecture will be stored in a common database to facilitate data access across current and future DSS modules.

In some embodiments, the system may also provide an application client to serve as a user interface for healthcare professionals. The client may provide interoperability and portability of the software across multiple computing platforms with the network and security constraints for specific operational settings (e.g. DoD healthcare institutions vs. civilian institutions).

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. A processor based method of supporting medical therapy decisions, the method comprising:
   receiving electronic medical record (EMR) data;
   predicting one or more data values from the EMR data at at least two future patient states from a current patient state;
   determining a weighted factor value of a weighted data type for each of the current patient state and the at least two future patient states;
   determining an unweighted factor value of an unweighted data type for each of the current patient state and the at least two future patient states;
   normalizing the weighted factor value and the unweighted factor value for each of the current patient state and the at least two future patient states as a risk index for each of the current patient state and the at least two future patient states; and
   normalizing the risk index for each of the current patient state and the at least two future patient states as an overall risk index.

2. The processor based method of claim 1 wherein the at least two future patient states comprise the future patient state at one, two, and three hours from the current patient state.

3. The processor based method of claim 1 wherein the EMR data comprises:
   a heart rate;
   a respiration rate;
   a systolic blood pressure;
   a mean arterial pressure;
   a temperature; and
   a urine output.

4. The processor based method of claim 3 wherein the EMR data further comprises:
   a blood glucose level;
   a white blood cell count;
   a creatinine level;
   a platelet count; and
   a lactate level.

5. The processor based method of claim 1 wherein the step of predicting one or more data values from the EMR data comprises predicting the one or more data values with a time-delay neural network model utilizing a history of EMR/patient-specific data and current data.

6. The processor based method of claim 5 wherein each EMR data source has a predictive model for each of the at least two future patient states.

7. The processor based method of claim 5 wherein the one or more data values from the EMR data comprises values of a diagnostic criteria for sepsis.

8. The processor based method of claim 1 further comprising determining a risk index value for a risk index.

9. The processor based method of claim 8 wherein the risk index comprises a Sepsis Risk Index (SRI) and the risk index value has a range from about 0 to about 100.

10. The processor based method of claim 9 where the SRI comprises a representation of a risk for a patient to acquire sepsis.

11. The processor based method of claim 1 wherein the weighted data type comprises one or more of the EMR data selected from the group consisting of: a heart rate; a respiration rate; a systolic blood pressure; a mean arterial pressure; a temperature; and a urine output.

12. The processor based method of claim 11 wherein the unweighted date type comprises one or more of the EMR data selected from the group consisting of:

a blood glucose level;
a white blood cell count;
a creatinine level;
a platelet count; and
a lactate level.

13. The processor based method of claim 1 further comprising determining a directive recommendation utilizing a Self-Organizing Feature Map (SOFM) wherein an input vector node based on the current patient state is mapped to a closest vector node of the SOFM to define the directive recommendation.

14. A processor based method of identifying a therapy risk, the method comprising:
   receiving electronic medical record (EMR) data comprising EMR data values of at least two EMR data types selected from the group consisting of:
      a heart rate,
      a respiration rate,
      a systolic blood pressure,
      a mean arterial pressure,
      a temperature,
      a urine output,
      a blood glucose level,
      a white blood cell count,
      a creatinine level,
      a platelet count, and
      a lactate level;
   predicting a first predicted value of each of the at least two EMR data types at a first time horizon with a time-delay neural network model utilizing the EMR data;
   comparing each of the first predicted values to a threshold for each of the at least two EMR data types;
   determining a first risk index value for each of the at least two EMR data types at the first time horizon; and
   normalizing each of the first risk index values to an overall risk index value.

15. The processor based method of claim 14 wherein the overall risk index is a sepsis risk index (SRI).

16. The processor based method of claim 14 wherein:
   one of the two EMR data types is a weighted data type; and
   the other EMR data type is an unweighted data type.

17. The processor based method of claim 14 further comprising:
   determining a current risk index value for each of the at least two EMR data types at a current time;
   predicting a second and third predicted value of each of the at least two EMR data types at a second and third time horizon respectively;
   comparing each of the second and third predicted values to the threshold for each of the at least two EMR data types;
   determining a second and third risk index value for each of the at least two EMR data types at the second and third time horizon respectively;
   normalizing each of the first risk index values to an overall risk index value comprises normalizing each of the current, the first, the second and the third risk index values to the overall risk index value whereby the overall risk index value identifies the therapy risk.

18. The processor based method of claim 14 further comprising determining a directive, recommendation utilizing a Self-Organizing Feature Map (SOFM) wherein an input vector node based on the current patient state is mapped to a closest vector node of the SOFM to define the directive recommendation.

19. A method for displaying medical information to support medical therapy decisions for a patient at a health care facility, the method comprising:
   dynamically displaying an electronic medical record (EMR) window configured to display EMR data values of EMR data the patient;
   dynamically displaying a predictive model window configured to display predicted EMR data values of the patient wherein the predicted EMR data values of the patient are determined with a time-delay neural network model utilizing a history of EMR/patient-specific data and current data;
   dynamically displaying a risk index window configured to display a risk index value; and
   dynamically displaying an access interface configured to provide access to an antibiogram of the health care facility.

20. The method of claim 19 wherein:
   the EMR data comprises one selected from the group consisting of:
      a heart rate,
      a respiration rate,
      a systolic blood pressure,
      a mean arterial pressure,
      a temperature, and
      a urine output; and
   the risk index is a sepsis risk index (SRI).

* * * * *